United States Patent
Baker, Jr. et al.

(10) Patent No.: US 10,532,170 B2
(45) Date of Patent: *Jan. 14, 2020

(54) METHOD AND SYSTEM FOR CLASSIFICATION OF PHOTO-PLETHYSMOGRAPHICALLY DETECTED RESPIRATORY EFFORT

(71) Applicant: Covidien LP, Mansfield, MA (US)

(72) Inventors: Clark R. Baker, Jr., Newman, CA (US); Michael P. O'Neil, Pleasanton, CA (US); Shannon E. Campbell, Boulder, CO (US); Gilbert Hausmann, Felton, CA (US)

(73) Assignee: COVIDIEN LP, Mansfield, MA (US)

( * ) Notice: Subject to any disclaimer, the term of this patent is extended or adjusted under 35 U.S.C. 154(b) by 1244 days.

This patent is subject to a terminal disclaimer.

(21) Appl. No.: 14/715,387

(22) Filed: May 18, 2015

(65) Prior Publication Data

US 2015/0246195 A1 Sep. 3, 2015

Related U.S. Application Data

(63) Continuation of application No. 13/757,564, filed on Feb. 1, 2013, now Pat. No. 9,044,558, which is a
(Continued)

(51) Int. Cl.
*A61M 16/00* (2006.01)
*A61B 5/0205* (2006.01)
(Continued)

(52) U.S. Cl.
CPC ....... *A61M 16/0069* (2014.02); *A61B 5/0205* (2013.01); *A61B 5/4818* (2013.01);
(Continued)

(58) Field of Classification Search
None
See application file for complete search history.

(56) References Cited

U.S. PATENT DOCUMENTS

| 4,106,503 A | 8/1978 | Rosenthal et al. |
| 4,365,636 A | 12/1982 | Barker |

(Continued)

FOREIGN PATENT DOCUMENTS

| DE | 9 200 422 | 7/1992 |
| EP | 0459284 B1 | 1/1995 |

(Continued)

OTHER PUBLICATIONS

Aboyans, V., et al., Sleep Apnoea Syndrome and the Extent of Atherosclerotic Lesions in Middle-Aged Men with Myocardial Infarction, International Angiology, Mar. 1999, vol. 18, No. 1, pp. 70-73.

(Continued)

*Primary Examiner* — Bradley H Philips
(74) *Attorney, Agent, or Firm* — Cantor Colburn LLP

(57) ABSTRACT

Embodiments disclosed herein may include systems and methods for determining a patient's respiratory effort and blood oxygen saturation based on data acquired from a pulse oximetry sensor and analyzing the parameters in conjunction with each other. For example, the respiratory effort may be determined based on a photo-plethysmographic waveform generated from light attenuation detected by the sensor, and the blood oxygen saturation may be a pulse-based estimate of arterial blood oxygen saturation determined from the detected attenuation. Analysis of the parameters may enable detection and classification of apnea (e.g., obstructive or central) or another underlying cause for respiratory instability. Furthermore, the measured respiratory effort may be compared to respiratory effort supplied by a ventilator to (Continued)

ensure proper sensor placement before enabling automatic adjustment of ventilator settings.

20 Claims, 3 Drawing Sheets

Related U.S. Application Data continuation of application No. 12/409,685, filed on Mar. 24, 2009, now Pat. No. 8,365,730.

(60) Provisional application No. 61/070,565, filed on Mar. 24, 2008.

(51) Int. Cl.
*A61B 5/00* (2006.01)
*A61B 5/024* (2006.01)
*A61B 5/1455* (2006.01)

(52) U.S. Cl.
CPC .... *A61M 16/0003* (2014.02); *A61M 16/0057* (2013.01); *A61B 5/02416* (2013.01); *A61B 5/1455* (2013.01); *A61B 5/726* (2013.01); *A61M 2205/18* (2013.01); *A61M 2205/33* (2013.01); *A61M 2205/50* (2013.01); *A61M 2230/20* (2013.01); *A61M 2230/205* (2013.01); *A61M 2230/40* (2013.01)

(56) References Cited

U.S. PATENT DOCUMENTS

| | | |
|---|---|---|
| 4,444,201 A | 4/1984 | Itoh |
| 4,523,279 A | 6/1985 | Sperinde |
| 4,630,614 A | 12/1986 | Atlas |
| 4,651,746 A | 3/1987 | Wall |
| 4,738,266 A | 4/1988 | Thatcher |
| 4,757,824 A | 7/1988 | Chaumet |
| 4,765,340 A | 8/1988 | Sakai et al. |
| 4,802,485 A | 2/1989 | Bowers et al. |
| 4,869,253 A | 9/1989 | Craig |
| 5,123,420 A | 6/1992 | Paret |
| 5,134,995 A | 8/1992 | Gruenke et al. |
| 5,199,424 A | 4/1993 | Sullivan |
| 5,206,807 A | 4/1993 | Hatke |
| 5,218,962 A | 6/1993 | Mannheimer et al. |
| 5,233,983 A | 8/1993 | Markowitz |
| 5,275,159 A | 1/1994 | Griebel |
| 5,303,699 A | 4/1994 | Bonassa et al. |
| 5,318,597 A | 6/1994 | Hauck et al. |
| 5,329,931 A | 7/1994 | Clauson et al. |
| 5,335,654 A | 8/1994 | Rapoport |
| 5,353,788 A | 10/1994 | Miles |
| 5,368,026 A | 11/1994 | Swedlow et al. |
| 5,385,144 A | 1/1995 | Yamanishi et al. |
| 5,398,682 A | 3/1995 | Lynn |
| 5,483,969 A | 1/1996 | Testerman |
| 5,485,851 A | 1/1996 | Erickson |
| 5,490,502 A | 2/1996 | Rapoport et al. |
| 5,535,739 A | 7/1996 | Rapoport et al. |
| 5,540,733 A | 7/1996 | Testerman et al. |
| 5,549,106 A | 8/1996 | Gruenke et al. |
| 5,551,419 A | 9/1996 | Froehlich et al. |
| 5,605,151 A | 2/1997 | Lynn |
| 5,632,270 A | 5/1997 | O'Mahony et al. |
| 5,645,053 A | 7/1997 | Remmers et al. |
| 5,645,054 A | 7/1997 | Cotner et al. |
| 5,682,878 A | 11/1997 | Ogden |
| 5,704,345 A | 1/1998 | Berthon-Jones |
| 5,730,144 A | 3/1998 | Katz et al. |
| 5,740,795 A | 4/1998 | Brydon |
| 5,743,250 A | 4/1998 | Gonda et al. |
| 5,749,900 A | 5/1998 | Schroeppel et al. |
| 5,751,911 A | 5/1998 | Goldman |
| 5,765,563 A | 6/1998 | Vander Schaaf |
| 5,769,082 A | 6/1998 | Perel |
| 5,769,084 A | 6/1998 | Katz et al. |
| 5,782,240 A | 7/1998 | Raviv et al. |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport et al. |
| 5,823,187 A | 10/1998 | Estes et al. |
| 5,827,179 A | 10/1998 | Lichter et al. |
| 5,830,135 A | 11/1998 | Bosque et al. |
| 5,845,636 A | 12/1998 | Gruenke et al. |
| 5,853,364 A | 12/1998 | Baker et al. |
| 5,865,173 A | 2/1999 | Froehlich |
| 5,865,736 A | 2/1999 | Baker, Jr. et al. |
| 5,891,022 A | 4/1999 | Pologe |
| 5,891,023 A | 4/1999 | Lynn |
| 5,902,250 A | 5/1999 | Verrier et al. |
| 5,944,680 A | 8/1999 | Christopherson et al. |
| 5,957,885 A | 9/1999 | Bollish |
| 6,006,379 A | 12/1999 | Hensley |
| 6,015,388 A | 1/2000 | Sackner et al. |
| 6,083,156 A | 7/2000 | Lisiecki |
| 6,105,575 A | 8/2000 | Estes et al. |
| 6,120,441 A | 9/2000 | Griebel |
| 6,138,675 A | 10/2000 | Berthon-Jones |
| 6,144,877 A | 11/2000 | DePetrillo |
| 6,148,814 A | 11/2000 | Clemmer et al. |
| 6,190,324 B1 | 2/2001 | Kieval et al. |
| 6,215,403 B1 | 4/2001 | Chan et al. |
| 6,216,032 B1 | 4/2001 | Griffin et al. |
| 6,223,064 B1 | 4/2001 | Lynn et al. |
| 6,286,508 B1 | 9/2001 | Remmers et al. |
| 6,299,581 B1 | 10/2001 | Rapoport et al. |
| 6,305,374 B1 | 10/2001 | Zdrojkowski et al. |
| 6,322,515 B1 | 11/2001 | Goor et al. |
| 6,342,039 B1 | 1/2002 | Lynn et al. |
| 6,345,619 B1 | 2/2002 | Finn |
| 6,360,114 B1 | 3/2002 | Diab et al. |
| 6,367,474 B1 | 4/2002 | Berthon-Jones et al. |
| 6,371,113 B1 | 4/2002 | Tobia et al. |
| 6,375,623 B1 | 4/2002 | Gavriely |
| 6,397,092 B1 | 5/2002 | Norris et al. |
| 6,401,713 B1 | 6/2002 | Hill et al. |
| 6,425,861 B1 | 7/2002 | Haberland et al. |
| 6,449,501 B1 | 9/2002 | Reuss |
| 6,463,326 B1 | 10/2002 | Hartley et al. |
| 6,488,634 B1 | 12/2002 | Rapoport et al. |
| 6,502,572 B1 | 1/2003 | Berthon-Jones et al. |
| 6,519,486 B1 | 2/2003 | Edgar, Jr. et al. |
| 6,529,752 B2 | 3/2003 | Krausman et al. |
| 6,532,960 B1 | 3/2003 | Yurko |
| 6,539,940 B2 | 4/2003 | Zdrojkowski et al. |
| 6,542,764 B1 | 4/2003 | Al-Ali et al. |
| 6,572,557 B2 | 6/2003 | Tchou et al. |
| 6,609,016 B1 * | 8/2003 | Lynn ............... C07C 233/36 600/323 |
| 6,609,517 B1 | 8/2003 | Estes et al. |
| 6,622,726 B1 | 9/2003 | Du |
| 6,637,434 B2 | 10/2003 | Noble |
| 6,640,806 B2 | 11/2003 | Yurko |
| 6,641,542 B2 | 11/2003 | Cho et al. |
| 6,661,161 B1 | 12/2003 | Lanzo et al. |
| 6,675,797 B1 | 1/2004 | Berthon-Jones |
| 6,684,090 B2 | 1/2004 | Ali et al. |
| 6,691,705 B2 | 2/2004 | Dittman et al. |
| 6,745,764 B2 | 6/2004 | Hickle |
| 6,748,252 B2 | 6/2004 | Lynn |
| 6,760,608 B2 | 7/2004 | Lynn |
| 6,761,167 B1 | 7/2004 | Nadjafizadeh et al. |
| 6,804,656 B1 | 10/2004 | Rosenfeld et al. |
| 6,807,965 B1 | 10/2004 | Hickle |
| 6,814,074 B1 | 11/2004 | Nadjafizadeh et al. |
| 6,817,361 B2 | 11/2004 | Berthon-Jones et al. |
| 6,822,564 B2 | 11/2004 | Al-Ali |
| 6,832,200 B2 | 12/2004 | Greevan et al. |
| 6,896,660 B2 | 5/2005 | Jelliffe et al. |
| 6,932,084 B2 | 8/2005 | Estes et al. |
| 6,948,497 B2 | 9/2005 | Zdrojkowski et al. |

(56) References Cited

U.S. PATENT DOCUMENTS

| | | | |
|---|---|---|---|
| 6,988,498 | B2 | 1/2006 | Berthon-Jones |
| 7,031,857 | B2 | 4/2006 | Tarassenko et al. |
| 7,123,950 | B2 | 10/2006 | Mannheimer |
| 7,153,263 | B2 | 12/2006 | Carter et al. |
| 7,225,013 | B2 | 5/2007 | Geva et al. |
| 7,297,119 | B2 | 11/2007 | Westbrook et al. |
| 7,309,314 | B2 | 12/2007 | Grant et al. |
| 7,398,115 | B2 | 7/2008 | Lynn |
| 7,417,124 | B2 | 8/2008 | Matsuzaki et al. |
| 2002/0117173 | A1 | 8/2002 | Lynn et al. |
| 2003/0100843 | A1 | 5/2003 | Hoffman |
| 2003/0158466 | A1 | 8/2003 | Lynn |
| 2004/0111014 | A1 | 6/2004 | Hickle |
| 2004/0163648 | A1 | 8/2004 | Burton |
| 2005/0016536 | A1 | 1/2005 | Rapoport et al. |
| 2005/0081854 | A1 | 4/2005 | Nadjafizadeh et al. |
| 2005/0113709 | A1 | 5/2005 | Millet |
| 2005/0119586 | A1 | 6/2005 | Coyle et al. |
| 2006/0189872 | A1 | 8/2006 | Arnold |
| 2007/0015976 | A1 | 1/2007 | Miesel et al. |
| 2007/0208269 | A1 | 9/2007 | Mumford et al. |
| 2007/0213620 | A1 | 9/2007 | Reisfeld |
| 2007/0213621 | A1 | 9/2007 | Reisfeld et al. |
| 2007/0213622 | A1 | 9/2007 | Reisfeld |
| 2007/0213624 | A1 | 9/2007 | Reisfeld et al. |
| 2008/0082018 | A1 | 4/2008 | Sackner et al. |
| 2008/0177195 | A1 | 7/2008 | Armitstead |
| 2008/0200775 | A1 | 8/2008 | Lynn |
| 2008/0257349 | A1 | 10/2008 | Hedner et al. |
| 2008/0269583 | A1 | 10/2008 | Reisfeld |
| 2009/0107502 | A1 | 4/2009 | Younes |
| 2010/0016694 | A1* | 1/2010 | Martin .............. A61M 16/0051 600/324 |
| 2014/0116442 | A1 | 5/2014 | Martin et al. |

FOREIGN PATENT DOCUMENTS

| | | |
|---|---|---|
| EP | 0651971 A1 | 10/1995 |
| EP | 0709107 A1 | 5/1996 |
| EP | 0714670 A2 | 6/1996 |
| EP | 0722747 A2 | 7/1996 |
| EP | 0788805 A3 | 5/1998 |
| EP | 0968734 A3 | 1/2000 |
| EP | 1004325 A3 | 6/2000 |
| EP | 0700690 B1 | 2/2002 |
| EP | 0759791 B1 | 8/2002 |
| EP | 0934723 B1 | 9/2004 |
| EP | 1172123 B1 | 10/2004 |
| EP | 0875258 B1 | 11/2004 |
| EP | 1488743 A2 | 12/2004 |
| WO | WO 88/01149 | 2/1988 |
| WO | WO 90/09146 | 8/1990 |
| WO | WO 90/14121 | 11/1990 |
| WO | WO 92/11054 | 7/1992 |
| WO | WO 92/22244 | 12/1992 |
| WO | WO 94/06499 | 3/1994 |
| WO | WO 94/23780 | 10/1994 |
| WO | WO 95/32016 | 11/1995 |
| WO | WO 97/14462 | 4/1997 |
| WO | WO 97/28838 | 8/1997 |
| WO | WO 99/24099 | 5/1999 |
| WO | WO 99/45989 | 9/1999 |
| WO | WO 00/67827 | 11/2000 |
| WO | WO 2004/047621 A2 | 6/2004 |
| WO | WO 2005/065757 A1 | 7/2005 |

OTHER PUBLICATIONS

Abraham, Howard et al., Sequential Cardiorespiratory Patterns in Septic Shock, Critical Care Medicine, vol. 11, No. 10, Oct. 1983, pp. 799-803.

Agilent Technologies, Agilent M1165/66/67/75/76/77A Component Monitoring System and Agilent M1205A V24 & V26, User's Reference Manual, vol. 1, System Information, Part No. M1046-9101L, First Ed., Printed Nov. 2000.

Agilent Technologies, Agilent M1165/66/67/75/76/77A Component Monitoring System and Agilent M1205A V24 & V26, User's Reference Manual, vol. 2, Parameter Information, Part No. M1046-9101L, First Ed., Printed Nov. 2000.

Aittokallio, Tero, et al., Analysis of Inspiratory Flow Shapes in Patients with Partial Upper-Airway Obstruction During Sleep, Chest, vol. 119, No. 1, Jan. 2001, pp. 37-44, Northbrook, IL, USA.

Alaris System, Brochure, Medication Safety System Focused at the Point of Care, Cardinal Health, Alaris Products, pp. 8.

Alchanatis, M., et al., Left ventricular function in patients with obstructive sleep apnoea syndrome before and after treatment with nasal continuous positive airway pressure, Respiration, 2000, vol. 67, No. 4, p. 367—(Abstract).

Andreas, Stefan, et al., Prevalence of Obstructive Sleep Apnoea in Patients with Coronary Artery Disease, Coronary Artery Disease, Jul. 1996, vol. 7, No. 7, pp. 541-545.

Attin, M. et al., *An Educational Project to Improve Knowledge Related to Pulse Oximetry*; American Journal of Critical Care, Nov. 2002, vol. 11, No. 6; pp. 529-534; US.

Aubry, et al., The $SaO_2/t$ Diagram as a Useful Means to Express Nocturnal Hypoxemia, Chest, 1989; 96: 1341-45.

Author Unknown, 1998 New Survey Reports More Than 168 Million American Adults Fail Sleep IQ Test, 132 Million Suffer Sleep Problems, Feb. 1998, Life Magazine.

Author Unknown, Background of Oximetry Utilization for Sleep Apnea Diagnosis, Publication information unknown, Undated.

Author Unknown, Chapter IV Oxygen Consumption During ADO, Introduction, pp. 40-46, Book Title Unknown, Date Unknown.

Author Unknown, Chapter X Effects of a 6-minute Period of ADO, Introduction, pp. 108-113, Book Title Unknown, Date Unknown.

Author Unknown, Guidance Article, (No Author), Critical Alarms and Patient Safety, Health Devices, vol. 31, No. 11, Nov. 2002, pp. 397-417, 2002 ECRI.

Author Unknown, Excessive Daytime Sleepiness, News Bulletin, http://www.websciences.org/nsf/ pressarchives/leadpressrelease_g.html, Jun. 3, 1997, Washington, DC, USA.

Author Unknown, News Bulletin, Lack of sleep America's top health problem, doctors say, Health Story Page, CNN, http://cnn.com/HEALTH/9703/17/nfm/sleep.deprivation/index.html, Mar. 17, 1997.

Author Unknown, Sleep Apnea & Heart Problems, News Channel WTVC, Chattanooga, Tennessee, USA, Jun. 3, 1999, News Bulletin.

Author Unknown, The Physiologic Parameters Defining the Oximetry Waveform Patterns in Sleep Apnea, Undated, Publication Unknown.

Author Unknown, The Ventilation Instability Detection Trial, Hospital Protocol, Early Discussion Draft, 4 pages, Facsimile dated Jul. 23, 2003, From SDC.

Ayas, Najib, et al., Unrecognized Severe Postoperative Hypercapnia: A Case of Apneic Oxygenation, Case Report, Mayo Clinic Proceedings, 1998, vol. 73, pp. 51-54, Minneapolis, Minnesota, USA.

Badoual, T., et al., Sleep Apnoea Syndrome and Cardiac Failure, Arch Mal Coeur Vaiss., Mar. 2005, vol. 98, No. 3, pp. 198-2, [Article in French] (Abstract).

BaHammam, A., Comparison of nasal prong pressure and thermistor measurements for detecting respiratory events during sleep, Respiration, Jul.-Aug. 2004, vol. 71, No. 4, pp. 385-390 (Abstract).

Baker, Clark R., et al., Nellcor 04 Algorithm Summary, Copyright 1999 Mallinckrodt Inc., pp. 1-8.

Ball, Eric M., et al., Diagnosis and Treatment of Sleep Apnea Within the Community, The Walla Walla Project, Arch Intern Med, vol. 157, Feb. 24, 1997, pp. 419-424.

Barach, Alvan L., et al., The Physiologic Action of Oxygen and Carbon Dioxide on the Coronary Circulation, as Shown by Blood Gas and Electrocardiographic Studies, The American Heart Journal, Received for publication Aug. 14, 1940, pp. 13-38.

Barker, Steven J., The Effects of Motion on the Performance of Pulse Oximeters in Volunteers (Revised Publication), Anesthesiology, Lippincott-Raven Publishers, American Society of Anesthesiologists, Inc.(Revised Publication) 1997, vol. 86, pp. 101-108 (Both paper and Abstract).

(56) References Cited

OTHER PUBLICATIONS

Barnum, P. T., et al., Novel Pulse Oximetry Technology Capable of Reliable Bradycardia Monitoring in the Neonate, Respiratory Care, 1997, vol. 42, No. 11, pp. 1072 (Abstract).
Bartolo, Anton, et al., An Arrhythmia Detector and Heart Rate Estimator for Overnight Polysomnography Studies, conditionally accepted for IEEE Transactions, 19 pages.
Bassetti, Claudio L., Sleep and Stroke, Seminars in Neurology, vol. 25, No. 1, Nov. 1, 2005, pp. 19-32.
Benumof, Jonathan L., Creation of Observational Unit May Decrease Sleep Apnea Risk, Letters to the Editor, Anesthesia Patient Safety Foundation Newsletter and posted on the Malpractice company's web site. The Doctors Company | Sleep Apnea and Narcotic Postoperative Pain, http://www.thedoctors.com/risk/bulletins/sleepapnea.asp.
Berg, Sören, et al., Continuous Intrathoracic Pressure Monitoring with a New Esophageal Microchip Catheter in Sleep-Related Upper Airway Obstructions, The Journal of Otolaryngology, vol. 24, No. 3, 1993, pp. 160-164.
Bernet-Buettiker, Vera et al., Evaluation of New Combined Transcutaneous Measurement of PCO2/Pulse Oximetry Oxygen Saturation Ear Sensor in Newborn Patients, Dec. 15, 2004, DOI: I0.1542/peds.2004-0946, Pediatrics Official Journal of the American Academy of Pediatrics, published online, pp. e-64-e68, Elk Grove Village, IL 60007, USA.
Berry, Richard B., Positive Nasal Airway Pressure Eliminates Snoring as Well as Obstructive Sleep Apnea, Chest, vol. 85, No. 1, Jan. 1984, pp. 15-20.
Berry, Richard B., et al., Comparison of Respiratory Event Detection by a Polyvinylidene Fluoride Film Airflow Sensor and a Pneumotachograph in Sleep Apnea Patients, Chest, The Cardiopulmonary and Critical Care Journal, Chest/128/3/Sep. 2005, pp. 1331-1338, Northbrook, IL, USA.
Berthon-Jones, M., et al., Time Course of Change in Ventilatory Response to $CO_2$ with Long-Term CPAP Therapy for Obstructive Sleep Apnea, American Review Respiratory Disease, 1987, vol. 135, pp. 144-147.
Berthon-Jones, Michael, Feasibility of a Self-Setting CPAP Machine, Sleep, vol. 16, pp. S120-S123, 1993.
Bixler, E. O., et al., Effects of age on sleep apnea in men: I. Prevalence and Severity, American Journal of Respiratory & Clinical Care Medicine, vol. 157, No. 1, pp. 144-148, Jan. 1998 (Abstract).
Blackshear et al., Nocturnal Dyspnea and Atrial Fibrillation Preset Cheyne-Stokes Respirations in Patients With Congestive Heart Failure, Jun. 26, 1995, Arch Intern Med. vol. 155, p. 1296-1302.
Blankfield, R. P., et al., Bilateral leg edema, obesity, pulmonary hypertension, and obstructive sleep apnea, Arch Intern Med., Aug. 14, 2000, vol. 28, 160(15), pp. 2357-2362 (Abstract).
Blankfield, R. P., et al., Bilateral leg edema, pulmonary hypertension, and obstructive sleep apnea: a cross-sectional study, Family Practice, Jun. 2002, vol. 51, No. 6, pp. 561-564 (Abstract).
Block, A. Jay, et al., Sleep Apnea, Hypopnea and Oxygen Desaturation in Normal Subjects, A Strong Male Predominance, The New England Journal of Medicine, vol. 300, Mar. 8, 1979, pp. 513-517.
Blumen, M., et al., Dilator muscles of the pharynx and their implication in the sleep apnea syndrome of obstructive type. Review of the literature, [Article in French], Ann Otolaryngol Chir Cervicofac, May 1998, p. 115, (Abstract).
Bock, A. V. et al., The Oxygen and Carbon Dioxide Dissociation Curves of Human Blood (This is study No. 37 of a series of studies on the physiology and pathology of blood form the Harvard Medical School and allied Hospitals, a part of the expense of which has been defrayed by the Proctor Fund for the study of chronic disease, Journal of Biologic Chemistry, vol. 29, 1924, pp. 353-377.
Bohnhorst, B., et al., Major Reduction in Alarm Frequency With a New Pulse Oximeter, Intensive Care Medicine, 1998, vol. 24, No. 3, pp. 277-278 (Abstract).
Bordier, P., et al., Death during polysomnography of a patient with cheyne-stokes respiration, respiratory acidosis, and chronic heart failure, Chest, Nov. 2004, vol. 126, No. 5, pp. 1698-1700 (Abstract).

Botelho, Ricardo Vieira, et al., Adult Chiari Malformation and Sleep Apnoea, Published online May 21, 2005, Neurosurgeon Review, vol. 28, pp. 169-176, 2005.
Boushra, N. N., Anaesthetic management of patients with sleep apnoea syndrome, Canadian Journal Anaesth, Jun. 1996, vol. 45, No. 6, pp. 599-616 (Abstract).
Bowton, David L., et al., The Incidence and Effect on Outcome of Hypoxemia in Hospitalized Medical Patients, The American Journal of Medicine, Vo. 97, Jul. 1994, pp. 38-46.
Bradley, Douglas T., et al., Daytime Hypercapnia in the Development of Nocturnal Hypoxemia in COPD, Chest, vol. 97, No. 2, Feb. 1990, pp. 308-312.
Brooks, L. J., et al., Adenoid size is related to severity but not the number of episodes of obstructive apnea in children, Journal of Pediatrics, vol. 132, No. 4, pp. 682-686, Apr. 1998 (Abstract).
Broughton, Roger J., et al., Practice Parameters for the Use of Stimulants in the Treatment of Narcolepsy, ASDA Standards of Practice, Sleep, vol. 17, No. 4, pp. 348-351, American Sleep Disorders Association and Sleep Research Society, 1994.
Brown, Lee K., "Dephlogisticated air" revisited: oxygen treatment for central sleep apnea, 1997 American College of Chest Physician, Physician Information, No. 8, Rev. 01, Nov. 1997.
Brown, D. L., et al., Screening for obstructive sleep apnea in stroke patients: a cost-effectiveness analysis, Stroke, Jun. 2005, pp. 1291-1293, Epub May 12, 2005 (Abstract).
Buckle, Patricia, et al., Polysomnography in Acutely Ill Intensive Care Unit Patients, Chest, v. 102 n. 1, p. 288 (4), American College of Chest Physicians.
Burk, John R., et al., Auto-CPAP in the Treatment of Obstructive Sleep Apnea: A New Approach, Sleep Research 21, 1992, p. 182, Abstract.
Cain, S. M., Breaking Point of Two Breath Holds Separated by a Single Inspiration, Journal of Appl. Physiol., vol. II(I), Jul. 1957, pp. 87-90.
Campos-Rodriguez, Francisco, et al., Mortality in Obstructive Sleep Apnea—Hypopnea Patients Treated With Positive airway Pressure, Chest, The Cardiopulmonary and Critical Care Journal, 2005, vol. 128, pp. 624-633, Northbrook, Illinois, USA (plus Abstract).
Cannesson, Maxime et al., Relation between respiratory variations in pulse oximetry plethsmographic waveform amplitude and arterial pulse pressure in ventilated patients, Critical Care 2005, vol. 9, #5, pp. R562-R568, Available online at, http://ccforum.com/content/9/5/R562.
Chaoquat, Ari, et al., Association of Chronic Obstructive Pulmonary Disease and Sleep Apnea Syndrome, American Journal Respiratory Critical Care Medicine, 1995, vol. 151, pp. 82-86.
Cherniack and Longobardo, Periodic Breathing During Sleep, pp. 158-190, New Jersey Medical School, Dean's Office, ID 9739727104, May 26, 1999, 14:23, No. 010, (first page missing).
Cherniack, N. S., Introduction to Session on the Pathophysiology of Breathing Control and Breathing: Awake and Asleep, Modeling and Control of Ventilation, Plenum Press, New York, USA, 1995, pp. 87-88.
Cherniack, N. S., New mechanisms for the cardiovascular effects of sleep apnea, American Journal Medicine, Nov. 1, 2000, vol. 109, No. 7, pp. 592-594 (Abstract).
Cherniack, Neil S., Oxygen Sensing: applications in humans, Highlighted Topic: Oxygen Sensing in Health and Disease, Journal Appl. Physiol., vol. 96, pp. 352-358, 2004, The American Physiological Society, http://www.jap.org.
Christiansen, J., et al., Carbon Dioxide in Blood, pp. 266-271, Proceedings of the Physiological Society, This Journal, XLVII, p. ii, 1913, pp. 266-271.
Cilli, Aykut, et al., Nocturnal Oxygen Desaturation in Coronary Artery Disease, JPN Heart Journal, Jan. 1999, pp. 23-28.
CNS Poly G, Printout Examples, CNS, Inc., Chanhassen, Minnesota, USA, Undated, Test Date Feb. 10, 1992.
Conte, G., et al., Acute cardiovascular diseases and respiratory sleep disorders, Minerva Cardioangiol, Jun. 1999, vol. 47, No. 6, pp. 195-202 (Abstract).
Cooper, B. G., et al., Value of Nocturnal Oxygen Saturation As a Screening Test for Sleep Apnoea, Thorax, 1991, vol. 46, pp. 586-588.

(56) References Cited

OTHER PUBLICATIONS

Coppola, Michael P., et al., Management of Obstructive Sleep Apnea Syndrome in the Home, The Role of Portable Sleep Apnea Recording, Chest, vol. 104, No. 1, Jul. 1993, pp. 19-24, Northbrook, IL, USA.
Coy, Timothy V., Sleep Apnoea and Sympathetic Nervous System Activity: A Review, Journal Slep Res., 1996, No. 5, pp. 42-50, European Sleep Research Society.
Daley, Denise M., MD, Beware of All Sedatives in Patients With Sleep Apnea, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp.
Decker, Michael J., et al., Ambulatory Monitoring of Arterial Oxygen Saturation, Chest, vol. 95, No. 4, Apr. 1989, pp. 717-722, Northbrook, Illinois, USA.
Deegan, P. C., et al., Predictive Value of Clinical Features for the Obstructive Sleep Apnoea Syndrome, European Respiratory Journal, vol. 9, pp. 117-124, 1996.
DeLeeuw, P.W., On sleep and death: cardiovascular risk the obstructive sleep apnea syndrome, Neth Journal Medicine, May 1999, vol. 54, No. 5, pp. 188-190 (Abstract).
Dement, William C., Chairman, National Commission on Sleep Disorders Research, Wake Up America: A National Sleep Alert, vol. 1, Executive Summary and Executive Report, Report of the National Commission on Sleep Disorders Research, Submitted to the United States Congress and to the Secretary, U.S. Department of Health and Human Services, Jan. 1993, pp. 1-76.
Demeter, P., et al., The relationship between gastroesophageal reflex disease and obstructive sleep apnea, Gastroenterology, Sep. 2004, vol. 39, No. 9, pp. 815-820 (Abstract).
Dempsey, Jerome A., et al., Sleep and Breathing State of the Art Review Sleep-Induced Breathing Instability, Sleep, vol. 19, No. 3, pp. 236-247, American Sleep Disorders Association and Sleep Research Society.
Den Herder, Cindy et al., Risks of general anaesthesia in people with obstructive sleep apnea, BMJ, vol. 329, Oct. 23, 2004, pp. 955-959, Downloaded from bmj.com.
Dhonneur, G., et al., Postoperative Obstructive Apnea, Anesth Analg., Sep. 1999, vol. 89, No. 3, pp. 762-767 (Abstract).
Doherty, L. S, et al., Long-term effects of nasal continuous positive airway pressure therapy on cardiovascular outcomes in sleep apnea syndrome, Chest, Jun. 2005, vol. 127, No. 6, pp. 2076-2084 (Abstract).
Douglass, Alan B., et al., The Sleep Disorders Questionnaire I: Creation and Multivariate Structure of SDQ, Clinical Research, Sleep, vol. 17, No. 1, pp. 160-167, 1994 American Sleep Disorders Association and Sleep Research Society.
Dowdell, WT; Javaheri, S; McGinnis, W, Cheyne-Stokes Respiration Presenting as Sleep Apnea Syndrome. Clinical and Polysomnographic Features, Am Rev Respir Dis, Apr. 1990, pp. 871-879.
Downs, John B., Has Oxygen Administration Delayed Appropriate Respiratory Care? Fallacies Regarding Oxygen Therapy, Respiratory Care, Jun. 2003, vol. 48, No. 6.
Downs, John B., Is Supplemental Oxygen Necessary, Journal of Cardiothoracic and Vascular Anesthesia, vol. 20, No. 2, Apr. 2006.
Dumas, Constantine, et al., Clinical Evaluation of a Prototype Motion Artifact Resistant Pulse Oximeter in the Recovery Room, Anesth Analg 1996, vol. 83, pp. 269-272.
Dursunoglu, D., et al., Impact of obstructive sleep apnoea on left ventricular mass and global function, European Respiratory Journal, Aug. 2005, vol. 26, No. 2, pp. 283-288 (Abstract).
Dyken, M. E., et al., Obstructive sleep apnea associated with cerebral hypoxemia and death, Neurology, Feb. 10, 2004, vol. 62, No. 3, pp. 491-493 (Abstract).
Dziewas, R., et al., Capnography screening for sleep apnea in patients with acute stroke, Neurology Res. Jan. 2005, vol. 27, No. 1, pp. 83-87 (Abstract).
Dziewas, R., et al., Increased Prevalence of Sleep Apnea in Patients with Recurring Ischemic stroke Compared with First Stroke Victims, Journal Neurology, Nov. 2005, vol. 252, No. 11, pp. 1394-1398. Epub Jul. 20, 2005 (Abstract).
Edge City Hospital Sleep Disorders Center, Sleep Summary of Patient, Houston, Texas, USA, pp. 1-3, Feb. 17, 1997.
Elfadel, I. M., et al., Motion-Resistant Pulse Oximetry, Abstract Only, Journal of Clinical Monitoring, vol. II, No. 4, Jul. 1995, p. 262.
Eihefnawy, Ahmed, et al., Stability Analysis of CO2 Control of Ventilation, Journal of Internal Medicine, 0161-7567/90, pp. 498-503, Publisher: The American Physiological Society, 1990.
Epstein et al., "Cost-Effectiveness Analysis of Nocturnal Oximetry As a Method of Screening for Sleep Apnea-Hypopnea Syndrome," Jan. 1, 1998, Chest, vol. 113, p. 97-103*.
Escourrou, P., et al., Heart failure and sleep respiratory disorders. Prevalence, physiopathology and treatment, [Article in French], Rev Mal Respir, Jun. 2000, vol. 17, Suppl 3, pp. S31-S40 (Abstract).
Evans, et al., A Microcomputer System for Monitoring and Analysing Oxyhemolobin Saturation During Sleep. Computer Programs in Biomedicine, 1984; 18: 227-234.
Farhi, Leon E., et al., Dynamics of Changes in Carbon Dioxide Stores, Anesthesiology, Nov.-Dec. 1960, vol. 21, pp. 604-614 (last page missing).
Farney, Robert J., et al., Ear Oximetry to Detect Apnea and Differentiate Rapid Eye Movement (REM) and Non-REM (NREM) Sleep, Screening for the Sleep Apnea Syndrome, Chest, vol. 89, No. 4, Apr. 1986, pp. 533-539, Northbrook, IL, USA.
Farre, R., et al., Importance of the Pulse Oximeter Averaging time When Measuring Oxygen Desaturation in Sleep Apnea, Sleep, Jun. 15, 1998, vol. 21, No. 4, pp. 386-390 Missing pp. 386 and 390.
Feinsilver, Steven H., Current and Future Methodology for Monitoring Sleep, Sleep Disorders, Clinics in Chest Medicine, vol. 19, No. 1, Mar. 1998, Published from the Division of Pulmonary Medicine, North Shore University Hospital, Manhasset, New York, NY, USA.
Ferber, Richard, et al., Portable Recording in the Assessment of Obstructive Sleep Apnea, ASDA Standards of Practice, American Sleep Disorders Association, 1610 14th Street, NW, Suite 300, Rochester, MN 55901-2200, USA.
Findley, Larry J., et al., Cheyne-Stokes Breathing During Sleep in Patients With Left Ventricular Heart Failure, Southern Medical Journal, vol. 78, No. 1, Jan. 1985, pp. 11-15.
Findley, Larry J., et al., Sleep Apnea and Auto Crashes, What is the Doctor to do?, Chest, vol. 94, No. 2, Aug. 1988, pp. 225-226.
Fisher, Kyle S., MD, Value of Pulse Oximetry Monitoring on the Ward is Questioned, Anesthesia Patient Safety Foundation Newsletter and posted on the Malpractice company's web site. The Doctors Company | Sleep Apnea and Narcotic Postoperative Pain, http://www.thedoctors.com/risk/bulletins/sleepapnea.asp.
Fiz, J. A., et al., Acoustic Analysis of Snoring Sound in Patients with Simple Snoring and Obstructive Sleep Apnoea, European Respiratory Journal, 1996, vol. 9, pp. 2365-2370, Printed in the United Kingdom.
Flemons, W. Ward, et al., Sleep Apnea and Cardiac Arrhythmias, Is There a Relationship?, American Review Respiratory Disease, vol. 148, pp. 618-621, 1993.
Fletcher et al., Effect of Cardiac Output Reduction on Rate of Desaturation in Obstructive Apnea; Chest, 99:452-456, 1991.
Fletcher et al., Rate of Oxyhemolglobin Desaturation in Obstructive versus Nonobstructive Apnea; Am Rev Respi Dis. 143:657-660; 1990.
Fletcher et al., The Rate of Fall of Arterial Oxyhemoglobin Saturation in Obstructive Sleep Apnea, Chest, 1989; 96: 717-722.
Fletcher, Eugene C., et al., Nocturnal Oxyhemoglobin Desaturation in COPD Patients with Arterial Oxygen Tensions Above 60 mm Hg, Chest, vol. 92, No. 4, Oct. 1987, pp. 604-608.
Forster, R. E., et al., Time course of exchanges between red cells and extracellular fluid during $CO_2$ uptake, Journal of Applied Physiology, vol. 38, No. 4, Apr. 1975, Printed in U.S.A.
Forster, Robert E., The Lung: Physiologic Basis of Pulmonary Function Tests (Book), 1986 Year Book medical Publishers, Inc., Chapter 3, I. Volume of Pulmonary Ventilation, pp. 32-64.

(56) References Cited

OTHER PUBLICATIONS

Franklin, C, et al.; "Developing strategies to prevent inhospital cardiac arrest: Analyzing responses of physicians and nurses in the hours before the event," *Critical Care Medicine*, vol. 22, No. 2, pp. 244-247, 1994.
Franklin, K. A., et al., Reversal of Central Sleep Apnea with Oxygen, Chest, Jan. 1997, vol. 111, No. 1, pp. 163-169 (Abstract).
Freid, E. B., The rapid sequence induction revisited: obesity and sleep apnea syndrome, Anesthesiol Clin North America, Sep. 2005, vol. 23, No. 3, pp. 551-564 (Abstract).
Frumin, Jack M., Apneic Oxygenation in Man, Anesthesiology, vol. 20, pp. 789-798, 1959.
Fu, Eugene S., et al., Supplemental Oxygen Impairs Detection of Hypoventilation by Pulse Oximetry, Chest 2004; vol. 126, pp. 1552-1558.
Gagnadoux, Fredrick et al., Home Unattended vs Hospital Telemonitored Polysomnography in Suspected Obstructive Sleep Apnea Syndrome: A Randomized Crossover Trial, Chest 2002; 121; pp. 753-758.
Gami, A. et al., Day-night pattern of sudden death in obstructive sleep apnea, New England Journal Medicine, Mar. 24, 2005, vol. 352, No. 12, pp. 1206-1214.
Gangitano, E. S., et al., Near Continuous Pulse Oximetry During Newborn ECLS, ASAI Journal, 1999, vol. 45, No. 1, p. 125 (Abstract).
Gaultier, C., Upper airway muscles and physiopathology of obstructive sleep apnea syndrome, [Article in French], Neurophysiol Clin, Jun. 1994, vol. 24, No. 3, pp. 195-206 (Abstract).
Gavin, T. P., et al., The effect of exercise modality on exercise-induced hypoxemia, Respiration Physiology, May 3, 1999, vol. 115, No. 3, pp. 317-323 (Abstract).
Gentil, Benoit, et al., Enhancement of Postoperative Desaturation in Heavy Snorers, Anesth Analg 1995, vol. 81, pp. 389-392.
George et al., Identification on Qualification of Apneas by Computer-based Analysis of Oxygen Saturation, American Review of Respiratory Disease, 1988; 137; pp. 1238-1240.
George, Charles Frederick Petersen, Diagnostic Techniques in Obstructive Sleep Apnea, Progress in Cardiovascular Diseases, vol. 41, No. 5, Mar./Apr. 1999, pp. 355-366.
Glerant, J. C., et al., Intensive care and respiratory sleep disorders, [Article in French], Rev Mal Respir, Dec. 1999, vol. 16, No. 6, pp. 1091-1104 (Abstract).
Gold, Avram R., et al., Impact of Basic Research on Tomorrow's Medicine, The Pharyngeal Critical Pressure, The Whys and Hows of Using Nasal Continuous Positive Airway Pressure Diagnostically, Chest, vol. 110, No. 4, Oct. 1996, pp. 1077-1088, Northbrook, IL, USA.
Goldberger, Ary L., et al., Components of a New Research Resource for Complex Physiologic Signals, PhysioBank, PhysioToolkit, and PhysioNet, American Heart Association Journals, Circulation, vol. 101, No. 23, pp. 1-9, 2000, Circulation, 2000:101:e215, http://circ.ahajournals.org/cgi/content/ful/101/23/e215.
Goldstein, M. R., et al., Pulse Oximetry in Transport of Poorly-Perfused Babies, Abstract only, Pediatrics, 1998, vol. 102, No. 3, p. 818.
Goode, Richard L., Who needs a sleep test? The value of the history in the diagnosis of obstructive sleep apnea, http://www.findarticles.com/p/articles/mi_m0BUM/is_9_78/ai_56229331/print, Sep. 1999.
Goodfriend, Theodore L., et al., Resistant Hypertension, Obesity, Sleep Apnea, and Aldosterone: Theory and Therapy, Hypertension, Journal of the American Heart Association, published online Jan. 19, 2004, Print ISSN: 0194-911X. Online ISSN: 1524-4563, pp. 518-524, Dallas, Texas, USA.
Grap, Mary Jo, Protocols for Practice, Applying Research at the Bedside, Critical Care Nurse, vol. 18, No. 1, Feb. 1998, pp. 94-99.
Greco, J. M., et al., Long-term Airway Space Changes after Mandibular Setback Using Bilateral Sagittal Split Osteomy, Internal Journal Oral Maxillofac. Surg. 1990, vol. 19, pp. 103-105.
Greco, Joan M., Cephalometric Analysis of Long-Term Airway Space Changes with Maxillary Osteotomies, Oral Surg Oral Med Oral Pathol, Nov. 1990, vol. 70, No. 5, pp. 552-554.
Griffiths, et al., A Video System for Investigating Breathing Disorders During Sleep, Thorad, 1991; 46: pp. 136-140.
Grimm, W., et al., Outcome of patients with sleep apnea-associated severe bradyarrhythmias after continuous positive airway pressure therapy, American Journal Cardiology, Sep. 15, 2000, vol. 86, No. 6, pp. 688-692 (Abstract).
Grote, Ludger, et al., Finger Plethysmography—A Method for Monitoring Finger Blood Flow During Sleep Disordered Breathing, Respiratory Physiology & Neurobiology, vol. 136, 2003, pp. 141-152, Publisher: Elsevier.
Grunstein, Ronald R., et al., Treatment of Sleep Disordered Breathing, Position Statement, The Medical Journal of Australia, vol. 154, Mar. 4, 1991, pp. 355-359, Australia.
Gugger, M., Comparison of ResMed AutoSet (version 3.03) with polysomnography in the diagnosis of the sleep apnoea/hypopnoea syndrome, European Respiratory Journal, Mar. 1997, vol. 10, No. 3, pp. 587-591 (Abstract).
Guilleminault et al., Sleep Apnea Syndrome: Can It Induce Hemodynamic Changes?, Western Journal of Medicine, vol. 123, Jul. 1975, pp. 7-16.
Guilleminault, C. et al., Unattended CPAP Titration: Toward a Smart Machine, May 20, Stanford University Sleep Research Center, 1 page.
Guilleminault, C., et al., Maxillo-mandibular surgery for obstructive sleep apnoea, European Respiratory Journal, 1989, vol. 2, pp. 604-612.
Guilleminault, C., et al., Sleep-disordered breathing in children, Annals of Medicine, vol. 30, No. 4, pp. 350-356, Aug. 1998 (Abstract).
Guilleminault, Christian, et al., A Cause of Excessive Daytime Sleepiness, The Upper Airway Resistance Syndrome, Chest, vol. 104, No. 3, Sep. 1993, pp. 781-787.
Guilleminault, Christian, et al., The Sleep Apnea Syndromes, Copyright 1976, Citation Annual Review of Medicine, vol. 27: 465-484 (volume publication date Feb. 1976).
Guilleminault, Christian, Obstructive Sleep Apnea, The Clinical Syndrome and Historical Perspective, Medical Clinics of North America, vol. 69, No. 6, Nov. 1985, pp. 1187-1203, Stanford, California, USA.
Gupta, R. M., et al., Perioperative cardiopulmonary evaluati and management: are we ignoring obstructive sleep apnea syndrome?, chest, Dec. 1999, vol. 116, No. 6, p. 1843 (Abstract).
Gupta, Rakesh M., et al., Postoperative Complications in Patients with Obstructive Sleep Apnea Syndrome Undergoing Hip or Knee Replacement: A Case-Control Study, Mayo Clinic Proceedings, 2001, vol. 76, pp. 897-905, Rochester, MN, USA.
Gyulay et al., A Comparison of Clinical Assessment and Home Oximetry in the Diagnosis of Obstructive Sleep Apnea, American Review of Respiratory Disease, 1993; 147: pp. 50-53.
Gyulay, Stephen, et al., Evaluation of a Microprocessor-Based Portable Home Monitoring System to Measure Breathing During Sleep, Sleep, vol. 10, No. 2, pp. 130-142, Raven Press, New York, USA, 1987, Association of Professional Sleep Societies.
Hanley, Patrick, et al., Pathogenesis of Cheyne-Stokes Respiration in Patients with Congestive Heart Failure, Relationship to Arterial Pco$_2$, Chest, vol. 104, No. 4, Oct. 1993, pp. 1079-1084.
Hanly, P. J., et al., Increased Mortality Associated with Cheyne-Stokes Respiration in Patients with Congestive Heart Failure, American Journal Respiratory Critical Care Medicine, Jan. 1996, vol. 153, No. 1, pp. 272-276 (Abstract).
Hanly, Patrick J., et al., Respiration and Abnormal Sleep in Patients with Congestive Heart Failure, Chest, vol. 96, No. 3, Sep. 1989, pp. 480-488.
Hanly, Patrick, et al., ST-Segment Depression During Sleep in Obstructive Sleep Apnea, The American Journal of Cardiology, vol. 71, Jun. 1, 1993, pp. 1341-1345.
Harbison, J., et al., Cardiac rhythm disturbances in the obstructive sleep apnea syndrome: effects of nasal continuous positive airway pressure therapy, Chest, Sep. 2000, vol. 118, No. 3, pp. 591— (Abstract).

(56) References Cited

OTHER PUBLICATIONS

Hatta, K., et al., Prolonged upper airway instability in the parenteral use of benzodiazepine with levomepromazine, Journal Clin Psychopharmacol, Feb. 2000, vol. 20, No. 1, pp. 99—(Abstract).
He, Jiang, et al., Mortality and Apnea Index in Obstructive Sleep Apnea, Experience in 385 Male Patients, Clinical Investigations, Chest, vol. 94, No. 1, Jul. 1988, pp. 9-14.
Health Devices, Next-Generation Pulse Oximetry, Special Issue, Feb. 2003, vol. 32, No. 2, Plymouth Meeting, PA, USA.
Henderson, L. J., et al., Blood as a Physicochemical System. II, pp. 426-431, Paper.
Hillman, David R., et al., Obstructive Sleep Apnoea and Anaesthesia, Sleep Medicine Reviews, 2004, vol. 8, pp. 459-472, Publisher: Elsevier.
Hoch, et al., Uberprufung der Fruherkennungsmethode MESAM und Biox 3700 zur Erfassung Schlafbezogener Atmmgmsergulationsstorungen bei jungen Mannern, Pneumologie, 1991; 45: pp. 217-222 (and translation).
Hoffarth, et al., Beuteilung Pulsoximetrisch Erfasster zklisheer . . and translation (Hoffarth et al. Assessment of Cyclic and Phasic Oxygen Desaturations Measured via Pulsoxymetry in Nocturnal Diagnosis of Respiratory Regulation Disorders, Peumologie, May 1991; 45: pp. 229-232.
Hoffman, Eric A., et al., Multimodality Imaging of the Upper Airway: MRI, MR Spectroscopy, and Ultrafast X-ray CT, Sleep and respiration, 1990 Wiley-Liss, Inc., pp. 291-301.
Hoffmann, M., et al., Sleep apnea and hypertension, Minerva Med., Aug. 2004, vol. 95, No. 4, pp. 281-290 (Abstract).
Hoffstein, Victor, Blood Pressure, Snoring, Obesity, and Nocturnal Hypoxaemia, The Lancet, vol. 344, Sep. 3, 1994, pp. 643-645.
Hoffstein, Victor, et al., Cardiac Arrhythmias, Snoring, and Sleep Apnea, Chest, 1994, vol. 106, pp. 466-471, Northbrook, IL, USA.
Hoffstein, Victor, et al., Snoring and Arousals: A Retrospective Analysis, Sleep, vol. 18, No. 10, pp. 866-882, 1995 American Sleep Disorders Association and Sleep Research Society.
Holmes, Michael, et al., Co-Oximetry Validation of a New Pulse Oximeter in Sick Newborns, Respiratory Care, 1998, vol. 43, No. 10, p. 860 (Abstract).
Howell, Mandy et al.; *Pulse oximetry: an audit of nursing and medical staff understanding*; British Journal of Nursing, 2002, vol. 11, No. 3; pp. 191-197.
Hornero, Roberto, et al.; "Utility of Approximate Entropy From Overnight Pulse Oximetry Data in the Diagnosis of the Obstructive Sleep Apnea Syndrome,"; *IEEE Transactions on Biomedical Engineering*, vol. 54, No. 1, pp. 107-113, Jan. 2007.
Hung, Joseph, et al., Association of Sleep Apnoea with Myocardial Interfarction in Men, The Lancet, vol. 336, pp. 261-264, Jul. 28, 1990, Abstract only, p. 261.
Isono, S., et al., Anatomy of pharynx in patients with obstructive sleep apnea and in normal subjects, Journal Appl Physiol, Apr. 1997, vol. 82, No. 4, pp. 1319-1326 (Abstract).
Isono, S., et al., Interaction of cross-sectional area, driving pressure, and airflow of passive velopharynx, Journal Appl Physiol, Sep. 1997, vol. 83, No. 3, pp. 851-859 (Abstract).
Isono, S., et al., Static mechanics of the velopharynx of patients with obstructive sleep apnea, Journal Appl Physiol, Jul. 1999, vol. 75, No. 1, pp. 148-154 (Abstract).
Jain, Sanjay S., et al., Perioperative Treatment of Patients with Obstructive Sleep Apnea, Current Opinion Pulmonary Medicine 10, pp. 482-488.
Jarrell, L., Preoperative diagnosis and postoperative management of adult patients with obstructive sleep apnea syndrome: a review of the literature, Journal Perianesth Nursing, Aug. 1999, vol. 14, No. 4, pp. 193-200 (Abstract).
Javaheri, S., Effects of continuous positive airway pressure on sleep apnea and ventricular irritability in patients with heart failure, Circulation, Feb. 1, 2000, vol. 101, No. 4, pp. 392-397 (Abstract).
Javaheri, S., et al., Occult Sleep-Disordered Breathing in Stable Congestive Heart Failure, Annuals Internal Medicine, Apr. 1995, vol. 122, No. 7, pp. 487-492 (Abstract).
Javaheri, S., et al., Sleep Apnea in 81 Ambulatory Male Patients With Stable Heart Failure, Types and Their Prevalences, Consequences, and Presentations, Received Nov. 20, 1997; revision received Jan. 23, 1998, accepted Jan. 28, 1998, From the Sleep Disorders Laboratory, Department of Veterans Affairs Medical Center, and the Deparment of Medicine, University of Cincinatti, College of Medicine, Cincinnati, Ohio.
Johnson, J. T., et al., Preoperative, Intraoperative, and postoperative management of patients with obstructive sleep apnea syndrome, Otolaryngol Clin North America, Dec. 1998, vol. 31, No. 6, pp. 1025-1030 (Abstract).
Jones, N. L., et al., The Estimation of Carbon Dioxide Pressure of Mixed Venous Blood During Exercise, Clinical Science (1967), vol. 32, pp. 311-327.
Juhász, János, et al., Unattended Continuous Positive Airway Pressure Titration, Clinical Relevance and Cardiorespiratory Hazards of the Method, American Journal Respiratory Critical Care Medical, vol. 154, pp. 359-365, 1996.
Kabeli, Cheryl, Obstructive Sleep apnea and Modifications in Sedation, Critical Care Nursing Clinics of North America, vol. 17, 2005, pp. 269-277, ccnursing.theclinics.com, Publisher: Elsevier Saunders.
Kalra, Maninder, et al., Obstructive Sleep Apnea in Extremely Overweight Adolescents Undergoing Bariatric Surgery, Obesity Research, vol. 13, No. 7, Jul. 2005, pp. 1175-1179.
Kanagala, Ravi, et al., Obstructive Sleep Apnea and the Recurrence of Atrial Fibrillation, Circulation, May 27, 2003, pp. 2589-2594, American Heart Association, Inc.
Kaplan, Joseph, Beginner's Atlas of Overnight Oximetry, Apr. 10, 1995, Mayo Clinic, Jacksonville, Florida, USA, Copyright 1986, PROFOX Associates, Inc.
Kaplan, Joseph, et al., Home Pulse Oximetry As a Screening Test for Sleep-Disordered Breathing, Chest, vol. 103, pp. 322S, (1993) Northbrook, IL, USA.
Kapur, V. K., et al., Association of hypothyroidism and obstructive sleep apnea, American Journal of Respiratory & Critical Care Medicine, vol. 158, No. 5 Pt. 1, pp. 1379-1383, Nov. 1998 (Abstract).
Kapur, V., et al., The medical cost of undiagnosed sleep apnea, Sleep, Sep. 1999, vol. 22, No. 6, pp. 749-755 (Abstract).
Katchen, Marc, et al., Evaluation of the Sleepy Crewmember: USAFSAM Experience and a Suggested Clinical Approach, Aviation, Space and Environmental Medicine, Mar. 1989, pp. 263-267.
Kaw, Roop, et al., Unrecognized Sleep Apnea in the Surgical Patient, Implications for the Perioperative Setting, Chest, 2006, vol. 129, pp. 198-205.
Kawai, Mitsuru, et al., Nocturnal hypoxia index: A new pulse oxymetry index of nocturnal hypoventilation in neuromuscular disorders, Clinical Neurology, vol. 35, pp. 1003-1007, 1995 (Abstract).
Keyl, C., et al., Spektralanalyse von Arterieller Sauerstoff-sattigung and RR-Intervallen bei Patienten mit obstrukitver Schlafapnoe, Wein Med Wschr 1995, pp. 515-516 (vol. 145).
Kimmel, Paul L., et al., Sleep Apnea syndrome in Chronic renal Disease, The American Journal of Medicine, vol. 86, Mar. 1989, pp. 308-314.
King, E. D., et al., A model of obstructive sleep apnea in normal humans. Role of the upper airway., American Journal Respiratory Critical Care Medicine, Jun. 2000, vol. 161, No. 6, pp. 1979-1984 (Abstract).
Kirby et al., Computer Quantitation of Saturation Impairment Time As an Index of Oxygenation During Sleep, Com Meth, 1992: 107-115.
Kirby, S.D., et al., Neural network prediction of obstructive sleep apnea from clinical criteria, Chest, vol. 116, No. 2, pp. 409-415, Aug. 1999 (Abstract).
Kirby, Stan C., et al., Section II. Systems and programs, Computer quantitation of saturation impairment time as an index of oxygenation during sleep, Computer Methods and Programs in Biomedicine, vol. 38, 1992, pp. 107-115, Elsevier Science Publishers B.V.
Klocke, F. J., et al., Breath holding after breathing of oxygen, Journal Appl. Physiol., vol. 14, No. 5, pp. 689-693, 1959.

(56) References Cited

OTHER PUBLICATIONS

Koehler, U. et al., Heart Block in Patients with Obstructive Sleep Apnoea: Pathogenetic Factors and Effects of Treatment, European Respiratory Journal, 1998, vol. 11, pp. 434-439, Printed in United Kingdom.
Koehler, U., et al., Nocturnal Myocardial Ischemia and Cardiac Arrhythmia in Patients with Sleep Apnea with and Without Coronary Heart Disease (1991) 69; 474-482.
Kolobow, Theodor, et al., Intratracheal Pulmonary Ventilation (ITPV); Control of Positive End-Expiratory Pressure at the Level of the Carina Through the Use of a Novel ITPV Catheter Design, Anesth Analg, 1994, vol. 78, pp. 455-461.
Koopmann, Charles F., et al., Surgical Management of Obstructive Sleep Apnea, Otolaryngologic Clinics of North America, vol. 23, No. 4, Aug. 1990, pp. 787-808.
Krachman, S. L., et al., Comparison of oxygen therapy with nasal continuous positive airway pressure on Cheyne-Stokes respiration during sleep in congestive heart failure, Chest, Dec. 1999, vol. 116, No. 6, pp. 1550-1557 (Abstract).
Kribbs, Nancy Barone, et al., Effects of One Night without Nasal CPAP Treatment on Sleep and Sleepiness in Patients with Obstructive Sleep Apnea, American Review Respiratory Disease, vol. 147, pp. 1162-1168, 1993.
Kribbs, Nancy Barone, et al., Objective Management of Patterns of Nasal CPAP Use by Patients with Obstructive Sleep Apnea, American Review Respiratory Disease, vol. 147, pp. 887-895, 1993.
Krieger, Jean, et al., Breathing During Sleep in Normal Middle-Aged Subjects, Sleep, vol. 13, No. 2, pp. 143-154, Raven Press, Ltd. New York, NY, USA, 1990 Association of Professional Sleep Societies.
Krieger, Jean, et al., Left Ventricular Ejection Fraction in Obstructive Sleep Apnea, Effects of Long-term Treatment with Nasal Continuous Positive Airway Pressure, Chest, vol. 100, No. 4, Oct. 1991, pp. 917-921.
Krieger, Jean et al., Dangerous Hypoxaemia During Continuous Positive Airway Pressure Treatment of Obstructive Sleep Apnoea, The Lancet, Dec. 17, 1983, pp. 1429-1430.
Kuna, S. T., et al., Pathophysiology of upper airway closure during sleep, JAMA, Sep. 11, 1991, vol. 266, No. 10, pp. 1384-1389 (Abstract).
Kyzer, S., et al., Obstructive Sleep Apnea in the obese, World Journal Surg, Sep. 1988, vol. 22, No. 9, pp. 998-1001 (Abstract).
Lafontaine, Victoria M., et al., Pulse Oximetry: Accuracy of Methods of Interpreting Graphic Summaries, Pediatric Pulmonology, vol. 21, 1996, pp. 121-131.
Lanfranchi, P. A., et al., Prognostic value of nocturnal Cheyne-Stokes respiration in chronic heart failure, Circulation, Mar. 23, 1999, vol. 99, No. 11, pp. 1435-1440, Italy (Abstract).
Lanfranchi, P., et al., The assessment of breathing during sleep: a curiosity or clinical necessity?, Italian Heart Journal, May 2000, vol. 1, No. 5 Suppl., pp. 641-654 (Abstract).
Lawrence, Nancy, Treatment for Sleep Apnea shows promise in reducing deaths from congestive heart failure: Nation-wide study to determine long-term benefits, London Health Sciences Centre, Jun. 3, 1999, News Bulletin.
Lertzman, Morley, et al., [Letters—Correspondence], Sleep Apnea a Risk Factor for Poor Driving, Canadian Medical Association Journal, Oct. 15, 1995; vol. 153(8), p. 1063.
Letters, Obstructive Sleep Apnoea, BMJ, 1997, pp. 315-367 (Aug. 9); http://bmj.com/Shneerson et al. (7104).
Lichstein, K. L., et al., Occult sleep apnea in a recruited sample of older adults with insomnia, Journal of Consulting & Clinical Psychology, vol. 67, No. 3, pp. 405-410, Jun. 1999 (Abstract).
Little, S. A., et al., Predictors of nocturnal oxygen desaturation in patients with COPD, Respir Med., Mar. 1999, vol. 93, No. 3, pp. 202-207, United Kingdom (Abstract).
Lofsky, Ann, Sleep Apnea and Narcotic Postoperative Pain Medication: A Morbidity and Mortality Risk, APSF Newsletter Summer 2002, pp. 24-25.

Longobardo et al., Sleep Apnea Considered as a Control System Instability, Sep. 1982, Respiratory Physiology 50: pp. 311-333.
Longobardo, G. S., et al., Sleep Apnea Considered As a Control System Instability, Elsevier Biomedical Press, 1982, 0034-5687/82/0000-0000.
Lowton, K., Pulse oximeters for the detection of hypoxaemia, Professional Nurse, Feb. 1999, vol. 14, No. 5, pp. 343-347 (Abstract).
Lugaresi, E., et al., Breathing During sleep in Man in Normal and Pathological Conditions, Proceedings of the Symposium on Regulation of Respiration during Sleep and Anesthesia held at the Faculte de Medecine Saint-Antoine, Paris, France, Jul. 14-16, 1977, 1978 Plenum Press, New York, USA, pp. 35-45.
Lynn, Lawrence A. et al., Diagnostic Evaluation of OSA Utilizing Analysis of Frequency and Spatial Relationships of Clustered, Sequential Oximetry Waveform Events, Vth World Congress on Sleep Apnea, Marburg, Germany, Sep. 17-20, 1997.
Lynn, Lawrence A., Cluster Analysis: A New Technology for the Evaluation of Oximetry and Airflow Waveforms in Obstructive Sleep Apnea, Accepted after revision on Dec. 20, 1997, 17 total pages.
Lynn, Lawrence, PROFOX Associates, Inc., Version 12S (12 hours SpO2), Demonstration disk for Dr. Lawrence Lynn, Columbus, Ohio, Copyright 1986 PROFOX Associates, Inc., Version 12S, Nov. 1992, p. 1.
Lynn, Lawrence A., Interpretive Oximetry: Future Directions for Diagnostic Applications of the $Sp0_2$ Time-Series, Anesth Analg 2002, vol. 94, pp. S84-S88.
Lynn, Lawrence; *Piercing the Panacea of Pulse Oximetry*; The Sleep and Breathing Research Institute, Columbus, Ohio, US.
Lyznicki, James M., Sleepiness, Driving and Motor Vehicle Crashes, JAMA, Jun. 17, 1998, vol. 279, No. 23, pp. 1908-1913.
Mackenzie, I.M.J.; *The haemodynamics of human septic shock*; Anaesthesia; 2001; 56; pp. 130-144; UK.
Magalang, Ulysses J. et al., Prediction of the Apnea-Hypopnea Index From Overnight Pulse Oximetry, Chest the Cardiopulmonary and Critical Care Journal, 2003; vol. 124; pp. 1694-1701, Northbrook, IL, USA.
Manley, G.T., Cerebral Oxygenation During Hemorrhagic Shock: Perils of Hyperventilation and the Therapeutic Potential of Hypoventilation, *J Trauma*: 2000; 48: 1025-1032.
Marin, José M., et al., Obstructive Sleep Apnea and Acute Myocardial Infarction: Clinical Implications of the Association, Sleep, vol. 21, No. 8, 1998, pp. 809-815.
Marin, Jose M., et al., Long-Term Cardiovascular Outcomes in Men with Obstructive sleep apnoea-hypopnoea with or without treatment with continuous positive airway pressure: an observational study, The Lancet, vol. 365, Issue 9464, Mar. 19, 2005-Mar. 25, 2005, pp. 1046-1053.
Mayer, Pierre, et al., Peripheral Neuropathy in Sleep Apnea, A Tissue Marker of the Severity of Nocturnal Desaturation, American Journal Respiratory Critical Care Medicine, vol. 159, pp. 213-219, 1999, Internet address: www.atsjournals.org.
McDannold, M. D., et al., Night-to-Night variability in Optimal CPAP Pressures Using Auto CPAP Titration in a Single Patient, Sleep Research No. 23, 1994, p. 453 (Abstract).
McEvoy, R. D., et al., Ventilatory responses to sustained eucapnic hypoxia in healthy males during wakefulness and NREM sleep, Sleep, vol. 20, No. 11, Nov. 1997, pp. 1008-1111 (Abstract).
McGregor, Christine D. et al., Performance of Pulse Oximeter Technologies in a Pediatric Sleep Lab Setting, OF-901-191, dated Nov. 2, 2001, Abstract.
McNicholas, W. T., et al., Diagnostic Criteria for the Sleep Apnoea Syndrome: Time for Consensus?, European Respiratory Journal, vol. 9, pp. 634-635, 1996, United Kingdom.
McQuillan, Peter, et al.; "Confidential inquiry into quality of care before admission to intensive care;" *BMJ*, vol. 316, pp. 1853-1858, Jun. 20, 1998.
Mehra, Reena, et al., Association of Nocturnal Arrhythmias with Sleep-Disordered Breathing: The Sleep Heart Health Study, AJRCCM Articles in Press, Published Jan. 19, 2006, as doi: 10.1164/rccm. 200509-1442OC, Copyright 2006 by the American Thoracic Society.

(56) References Cited

OTHER PUBLICATIONS

Mehta, Y., et al., Obstructive sleep apnea syndrome: anesthetic implications in the cardiac surgical patient, Journal Cardiothorac Vasc Anesth, Aug. 2000, vol. 14, No. 4, pp. 449-453 (Abstract).
Mendelson, W. B., et al., Effects of Hemodialysis on Sleep Apnea Syndrome in End-Stage Renal Disease, Clinical Nephrology, vol. 33, No. 5, 1990, pp. 247-251.
Middlekoop, Huub, et al., The Value of Nocturnal Motor Activity Monitoring as a Screening Tool for Obstructive Sleep Apnoea, Letter to the Editor, Journal Sleep Res., 1996, vol. 5, pp. 66-67.
Miles, L. E., et al., Development and Application of Automatic Nasal CPAP Calibration Procedures for Use in the Unsupervised Home Environment, Sleep, vol. 16, pp. S118-S119, 1993 American Sleep Disorders Association and Sleep Research Society.
Miles, Laughton E., Optimization of Nasal-CPAP Airflow Pressure by Use of Home Oximetry Recordings, Clinical Monitoring Center, Palo Alto, California, USA, Sleep Research, p. 568, 1987, Abstract.
Millard, R. K., Inductive plethysmography components analysis and improved non-invasive postoperative apnoea monitoring, Physiol Meas, May 1999, vol. 20, No. 2, pp. 175-186, United Kingdom (Abstract).
Mitler, Merrill M., et al., Narcolepsy and Its Treatment With Stimulants, ASDA Standards of Practice, Sleep, vol. 17, No. 4, pp. 352-371, 1994, American Sleep Disorders Association and Sleep Research Society.
Miyamura, Miharu, et al., $CO_2$ Dissociation Curves of Oxygenerated Whole Blood Obtained at Rest and in Exercise, European Journal Applied Physiology, vol. 39, pp. 37-45, 1978, European Journal of Applied Physiology and Occupation Physiology.
Moller, J.T. et al.; *Hypoxaemia is Reduced by Pulse Oximetry Monitoring in the Operating Theatre and in the Recovery Room*; British Journal of Anaesthesia; 1992; vol. 68; pp. 146-150.
Moller, Jakob T. et al.; *Randomized Evaluation of Pulse Oximetry in 20,802 Pateints: I*; Anesthesiology, vol. 78, No. 3; Mar. 1993; pp. 436-444; US.
Moller, Jakob T. et al.; *Randomized Evaluation of Pulse Oximetry in 20,802 Patients: II*; Anesthesiology, vol. 78, No. 3; Mar. 1993; pp. 445-453; US.
Morelot-Panzini, Capucine et al., Simplified Method to Measure Respiratory-Related Changes in Arterial Pulse Pressure in Patients Receiving Mechanical Ventilation, Chest 2003, vol. 124, pp. 665-670, Northbrook, IL, USA.
Muller, Nestor L., et al., Mechanism of Hemoglobin Desaturation During Rapid-Eye-Movement Sleep in Normal Subjects and in Patients with Cystic Fibrosis, American Review of Respiratory Disease, vol. 121, 1980, pp. 463-469.
Murray, Carol B. et al.; *Making the most of pulse oximetry*; Contemporary Pediatrics; Jul. 1995; pp. 45-62.
Myatt, H. M., et al., Snoring—a simple surgical solution, Clin. Otolaryngol., 1996, vol. 21, pp. 419-424, Publisher: Blackwell Science Ltd.
Narkiewicz, Krzysztof, et al., Altered Cardiovascular Variability in Obstructive Sleep Apnea, Copyright 1998, American Heart Association, Inc., Iowa City, Iowa, USA, pp. 1071-1077, Published Sep. 15, 1998.
Naughton, Matthew T., et al., Sleep Apnea in Congestive Heart Failure, Clinics in Chest Medicine, vol. 19, No. 1, Mar. 1998, pp. 99-113.
Naughton, Matthew T., Cycling Sleep Apnea, The Balance of Compensated and Decompensated Breathing, American Journal of Respiratory and Critical Care Medicine, vol. 168, 2003, Editorials, pp. 624-625.
Neuman, Michael R.; *Pulse Oximetry: Physical Principles, Technical Relization and Present Limitations*; Adv Exp Med Biol 1987;220; pp. 135-144.
Neumann, Cristina et al., Nocturnal oxygen desaturation in diabetic patients with severe autonomic neuropathy, Diabetes Research and Clinical Practice, Publisher: Elsevier Science Ireland Ltd, vol. 28, 1995, pp. 97-102.

Netzer, Nikolaus, et al., Overnight Pulse Oximetry for Sleep-Disordered Breathing in Adults, A Review, Chest, vol. 120, #2, Aug. 2001, pp. 625-633, Northbrook, IL, USA.
Nobili, L., et al., Morning increase of whole blood viscosity in obstructive sleep apnea syndrome, Clinical Hemorheol Microcirc, 2000, vol. 22, No. 1, pp. 21-27 (Abstract).
Noda, A., et al., Daytime sleepiness and automobile accidents in patients with obstructive sleep apnea syndrome, Psychiatry & Clinical Neurosciences, vol. 52, No. 2, pp. 221-222, Apr. 1988 (Abstract).
Noda, Akiko, et al., Circadian Rhythm of Autonomic Activity in Patients with Obstructive Sleep Apnea Syndrome, Clinical Cardiology, vol. 21, pp. 271-276, 1998, Japan.
O'Donovan, Richard et al.; *Acid-Base Disturbances in Cardiogenic Polmonart Edema*; Nephron; 1991; 57; pp. 416-420.
Ogan, O. U., et al., Anesthetic safety always an issue with obstructive sleep apnea, Journal Clin Monit Comput, Jan. 1998, vol. 14, No. 1, pp. 69-70 (Abstract).
Ogretmenoglu, O., et al., Body fat composition: a predictive factor for obstructive sleep apnea, Laryngoscope, Aug. 2005, vol. 115, No. 8, pp. 1493-1498 (Abstract).
Ohga, Eijiro, et al., Increased Levels of Circulating ICAM-1, VCAM-1, and L-selectin in obstructive sleep apnea syndrome, Address for reprint requests and other correspondence: T. Nagase, Dept. of Geriatric Medicine, Faculty of Medicine, Univ. of Tokyo, 7-3-1, Hongo, Bunkyo-Ku, Tokyo 113, Japan, Received Nov. 13, 1998, accepted in final form Mar. 9, 1999.
Olson, L. G., et al., Prediction of Sleep-disordered breathing by unattended overnight oximetry, Journal Sleep Res., 1999, vol. 8, pp. 51-55, European Sleep Research Society.
Olson, Leslie G., et al., Chapter 10, A Biomechanical View of Upper Airway Function, pp. 359-389, 1988, Publisher, Marcel Dekker, Inc., New York-Basel, Book: Respiratory Function of the Upper Airway.
Ostermeier, A. M., et al., Three sudden postoperative respiratory arrests associated with epidural opioids in patients with sleep apnea, Anasth Analg., Aug. 1997, vol. 85, No. 2, pp. 452-460.
Owen, G. O., et al., Overnight Pulse Oximetry in Normal Children and in Children Undergoing Adenotonsillecomy, Clinical Otolaryngology, 1996 vol. 21, pp. 59-65, Blackwell Science Ltd.
Owen, G. O., et al., Overnight Pulse Oximetry in Snoring and Non-Snoring Children, Clinical Otolaryngology, 1995, vol. 20, pp. 402-406, Blackwell Science Ltd.
OxiScan, AirSep Corporation, 800/874-0202, Oxiscan Sample Report/ Explanation and the Delta Sleep Apnea Index, OxiScan Sample Report, vol. 1, Rev. 01, Nov. 1997.
Pae, E. K., et al., Intermittent hypoxia damages cerebellar cortex and deep nuclei, Neurosci Lett., Feb. 28, 2005, vol. 375, No. 2, pp. 123-128 (Abstract).
Partinen, Markku, et al., Daytime Sleepiness and Vascular Morbidity at Seven-Year Follow-up in Obstructive Sleep Apnea Patients, Chest, vol. 97, No. 1, Jan. 1990, pp. 27-32.
Patil, Ramesh S. et al., Application of an Artificial Intelligence Program to Therapy of High-Risk Surgical Patients, New Horizons, vol. 4, No. 4, pp. 541-550.
Payne, J. P., Apnoeic Oxygenation in Anaesthetised Man, Acta Anaesth. Scandinav., 1962, vol. 6, pp. 129-142.
Peker, Y., et al., An independent association between obstructive sleep apnoea and coronary artery disease, European Respiratory Journal, 1999, vol. 14, No. 1, pp. 179-184 (Abstract).
Peker, Y., et al., Reduced hospitalization with cardiovascular and pulmonary disease in obstructive sleep apnea patients on nasal CPAP treatment, Sleep, 1997, vol. 20, No. 8, pp. 45-53 (Abstract).
Peled, N., et al., Nocturnal ischemic events in patients with obstructive sleep apnea syndrome and ischemic heart disease: effects of continuous positive air pressure treatment, Journal American Coll Cardiology, Nov. 1999, vol. 15, p. 34 (Abstract).
Pelttari, Lisa H., et al., Little Effect of Ordinary Antihypertensive Therapy on Nocturnal High Blood Pressure in Patients with Sleep Disordered Breathing, American Journal of Hypertension, 1998, vol. 11, No. 3, Part 1, pp. 272-279.

(56) References Cited

OTHER PUBLICATIONS

Penzel, T., et al., Systematic Comparison of Different Algorithms for Apnoea Detection Based on Electrocardiogram Recordings, Medical & Biological Engineering and Computing 2002, vol. 40, pp. 402-407.
Pepin et al., Does Oximetry contribute to the Detection of Apneic Events? Mathematical. Processing of the $SaO_2$ Signal, Chest, May 1991; 99: pp. 1151-1157.
Peppard, Paul E., et al., Prospective Study of the Association Between Sleep-Disordered Breathing and Hypertension, May 11, 2000, vol. 342, No. 19, pp. 1378-1384.
Peters, John P. Jr., et al., Studies of the Carbon Dioxide Absorption Curve of Human Blood, Book: The Journal of Biological Chemistry, pp. 709-716, Received for publication, Feb. 7, 1923.
Peters, John P. Jr., et al., The Carbon Dioxide Absorption Curve and Carbon Dioxide Tension of the Blood of Normal Resting Individuals, Book: Carbon Dioxide Absorption Curve, pp. 489-547, Received for publication, Dec. 2, 1920 (missing pp. 490, 491, 538-541).
Phillips, Barbara A., et al., Catching Up on Sleep, The National Sleep Disorders Research Plan, Editorial, Chest, vol. 110, No. 5, Nov. 1996, pp. 1132-1133.
Phillips, Susan, et al., Obstructive Sleep Apnoea: Diagnosis and Management, Nursing Standard, vol. 11, No. 17, pp. 43-46, 1997.
Phillipson, Eliot A., Sleep Apnea—A Major Public Health Problem, Editorials, The New England Journal of Medicine, Editorials, vol. 328, No. 17, pp. 1271-1273, Apr. 29, 1993/.
Plastiras, James, Sleep disorders create need for more sleep labs, Capital District Business Review, Mar. 9, 1998/.
Poets, C. F., et al., Arterial oxygen saturation and breathing movements during the first year of life, Journal Developmental Physiology, Jun. 1991, vol. 15, No. 6, pp. 341-345 (Abstract)/.
Poets, C. F., et al., Home monitoring of transcutaneous oxygen tension in the early detection of hypoxaemia in infants and young children, Arch Dis Child, Jun. 1991, vol. 66, No. 6, pp. 676-682 (Abstract).
Poets, C. F., et al., Oxygen saturation and breathing patterns in infancy. 2: Preterm infants at discharge from special care, Arch Dis Child, May 1991, vol. 66, No. 5, pp. 574-578 (Abstract).
Poets, C. F., et al., Patterns of oxygenation during periodic breathing in preterm infants, Early Human Development, Jul. 1991, vol. 26, No. 1, pp. 1-12 (Abstract).
Poets, C. F., Apparent life-threatening events and sudden infant death on a monitor, Paediatr Respiratory Review, 2004, Suppl. A, pp. S383-S386 (Abstract).
Pradhan, Pratik S., et al., Screening for Obstructive Sleep Apnea in Patients Presenting for Snoring Surgery, Laryngoscope, vol. 106, Nov. 1996, pp. 1393-1397.
Principe-Rodriguez, K., et al., Sleep symptoms and clinical markers of illness in patients with heart failure, Sleep Breath., Sep. 2005, vol. 9, No. 3, pp. 127-133 (Abstract).
Quinn, S. J., et al., The Differentiation of Snoring Mechanisms Using Sound Analysis, Clinical Otolaryngol., 1996, vol. 21, pp. 119-123, Publisher: Blackwell Science Ltd.
Randerath, Winfried J., et al., Autoadjusting CPAP Therapy Based on Impedance Efficacy, Compliance and Acceptance, American Journal Respiratory Critical Care Medicine, vol. 163, pp. 652-657, 2001, Internet address: www.atsjournals.org.
Rapoport, David M., et al., Reversal of the "Pickwickian Syndrome" by Long-Term Use of Nocturnal Nasal-Airway Pressure, The New England Journal of Medicine, Oct. 7, 1982, vol. 307, No. 15, pp. 931-933.
Rapoport, et al., CO2 Homeostasis During Periodic Breathing: Predictions From a Computer Model, The American Journal of Applied Physiological, 1993, vol. 75, Issue 5, pp. 2302-2309.
Rauscher et al., Computerized Detection of Respiratory Events During Sleep from Rapid Increases in Oxyhemoglobin Saturation, Lung, 1991; 169: pp. 355-42.
Rauscher et al., Quantification of sleep-disordered breathing by computerized analysis of oximetry, heart rate, and snoring, Eur Respir J. Jun. 1991; 4: pp. 655-659.
Rauscher, Helmuth, et al., Computerized Detection of Respiratory Events During Sleep from Rapid Increases in Oxyhemoglobin Saturation, Lung, 1991, vol. 169, pp. 335-342.
Redline, Susan, et al., Hypopnea, a Floating Metric: Implications for Prevalence, Morbidity Estimates, and Case Finding, Sleep, vol. 20, No. 12, pp. 1209-1217 (1997).
Redline, Susan, et al., Recognition and Consequences of Obstructive Sleep Apnea Hypopnea Syndrome, Sleep Disorders, Clinics in Chest Medicine, vol. 19, No. 1, Mar. 1998, Cleveland, Ohio, USA (Article and Abstract).
Reite, Martin, et al., The Use of Polysomnography in the Evaluation of Insomnia, An American Sleep Disorders Association Review, Sleep, vol. 18, No. 1, 1995, pp. 58-70, American Sleep Disorders Association and Sleep Research Society 1995.
Remmers, John E., et al., Nasal Airway Positive Pressure in Patients with Occlusive Sleep Apnea, Methods and Feasibility, American Review Respiratory Disorders, Dec. 1984, vol. 130, No. 6, pp. 1152-1155.
Rennotte, M. T., Epidural opioids and respiratory arrests, Anesth Analg., Aug. 1997, vol. 85, No. 2, pp. 452-460 (Abstract).
Resta, O., et al., Sleep-related breathing disorders in acute respiratory failure assisted by non-invasive ventilatory treatment: utility of portable polysomnographic system, Respir Medicine, Feb. 2000, vol. 94, No. 2, pp. 128-134 (Abstract).
Riley, Robert W., et al., Maxillofacial Surgery and Nasal CPAP, A Comparison of Treatment for Obstructive Sleep Apnea Syndrome, Chest, vol. 98, No. 6, Dec. 1990, pp. 1421-1425.
Riley, Robert W., et al., Maxillofacial Surgery and Obstructive Sleep Apnea: A Review of 80 Patients, Otolaryngology—Head and Neck Surgery, vol. 101, No. 3, Sep. 1989, pp. 353-361.
Riley, Robert W., et al., Maxillofacial Surgery and Obstructive Sleep Apnea Syndrome, Otolaryngologic Clinics of North America, vol. 23, No. 4, Aug. 1990, pp. 809-824.
Rosenberg, J., et al., Ventilatory Pattern and Associated Episodic Hypoxaemia in the Late Postoperative Period in the General Surgical Ward, Anaesthesia, 1999, vol. 54, pp. 323-328, Publisher: Blackwell Science Ltd.
Roux, Francoise, et al., Sleep-related Breathing Disorders and Cardiovascular Disease, The American Journal of Medicine, Apr. 1, 2000, vol. 108, pp. 396-400.
Ruchala, Joanna B., Chapter 13, Applications of Pulse Oximetry, Book: Design of Pulse Oximeters, pp. 214-236.
Ruhle, K. H., et al., Monitoring at Home, Lung, 1990, Suppl, pp. 927-932, Lung, Springer-Verlag, New York, Inc. 1990.
Rundell, O. H., et al., Polysomnography Methods and Interpretations, Sleep Apnea, Otolaryngologic Clinics of North America, vol. 23, No. 4, Aug. 1990, pp. 583-592.
Rusch, T. L., et al., Signal Processing Methods for Pulse Oximetry, Computers in Biology & Medicine, vol. 26, No. 2, pp. 143-159, Mar. 1996 (Abstract).
Ryan, C. Francis, et al., Mechanical Properties of the Velopharynx in Obese Patients with Obstructive Sleep Apnea, American Journal Respiratory Critical Care Medicine, 1996, vol. 154, pp. 806-812.
Ryan, Clodagh M., et al., Periodicity of Obstructive Sleep Apnea in Patients With and Without Heart Failure, Chest 2005; 127, pp. 536-542.
Saarelainen, Seppo, et al., Effect of Nasal CPAP Treatment on Plasma Volume, Aldosterone and 24-h Blood Pressure in Obstructive Sleep Apnoea, Journal Sleep Research, 1996, vol. 5, pp. 181-185.
Sadeh, Avi, et al., The Role of Actigraphy in the Evaluation of Sleep Disorders, An American Sleep Disorders Association and Sleep Research Society, Sleep, vol. 18, No. 4, pp. 288-302.
Sadrmoori, Bijan, Evaluation of Self Adjusting Nasal CPAP (DPAP) in the Treatment of Adult Obstructive Sleep Apnea, Sleep Research No. 23, 1994, p. 386 (Abstract).
Saito, Toshiyuki, et al., Sleep Apnea in Patients with Acute Myocardial Infarction, Critical Care Medicine, vol. 19, No. 7, pp. 938-941, Printed in USA, Copyright 1991 by Williams and Wilkins.
Sajkov, Dimitar, et al., Daytime Pulmonary Hemodynamics in Patients with Obstructive Sleep Apnea without Lung Disease, American Journal Respiratory Critical Care Medicine, 1999, vol. 159, pp. 1518-1526.

(56) References Cited

OTHER PUBLICATIONS

Salmi, et al., Evaluation of Automatic Analysis of SCSB, Airflow and Oxygen Saturation Signals in Patients with Sleep Related Apneas, Chest, 1989; 96: pp. 255-261.

Sanders, Mark H., et al., Obstructive Sleep Apnea Treated by Independently Adjusted Inspiratory and Expiratory Positive Airway Pressures via Nasal Mask, Physiologic and Clinical Implications, Chest, vol. 98, No. 2, Aug. 1990, pp. 317-324.

Sanders, Mark H., Nasal CPAP Effect on Patterns of Sleep Apnea, Chest, vol. 86, No. 6, Dec. 1984, pp. 839-844.

Sangal, R. Bart et al., P300 Latency: Abnormal in Sleep Apnea with Somnolence and Idiopathic Hypersomnia, but Normal in Narcolepsy, Clinical Electroencephalography, 1995, vol. 26, No. 3, pp. 146-153, Troy, Michigan, USA.

Sanna, A., et al., Apport de la Polysomnographie à la mise au point des maladies atteints d'une bronchopneumopathie chronique obstructive (BPCO), Travail Original, Rev. Mèd. Brux., vol. 12, pp. 315-320, 1991, Belgium.

Sanner, B. M. et al., Sleep-related respiration disorders: their relevance in intensive care medicine, [Article in German], Dtsch Med Wochenschr, Mar. 1999, vol. 12, p. 124 (Abstract).

Sarodia, B.D., et al., Prevalence of obstructive sleep apnea in patients admitted to the intensive care unit with cardiovascular events, Sleep Research, 1996, vol. 25, pp. 356.

Schafer, H., et al., Cardiovascular morbidity in patients with obstructive sleep apnea in relation to the severity of respiratory disorder, Dtsch Med Wochenschr, 1998, vol. 123, No. 39, pp. 1127-1133 (Abstract).

Schafer, H. et al., Pulmonary Haemodynamics in Obstructive Sleep Apnoea: Time Course and Associated Factors, European Respiratory Journal, 1998, vol. 12, pp. 679-684, Printed in United Kingdom.

Schagatay, E., et al., Diving Response and Apneic Time in Humans, Undersea Hyper Med., 1998, vol. 25, No. 1, pp. 13-19, Copyright 1988 Underseas and Hyperbaric Medical Society, Inc.

Scharf, Martin B., et al., Cyclic Alternating Pattern Sequences in Non-Apneic Snorers With and Without Nasal Dilation, ENT-Ear, Nose & Throat Journal, Sep. 1996, vol. 75, No. 9, pp. 617-619.

Scharf, Steven M., et al., Cardiovascular Effects of Periodic Occlusions of the Upper Airways in Dogs, American Review of Respiratory Disease, pp. 321-329.

Scheers, N. J., et al., Sudden Infant Death With External Airways Covered, Case-Comparison Study of 206 Deaths in the United States, Arch Pediatric Adolescent Medicine, 1998, vol. 152, pp. 540-547.

Schein, R. M., et al., Clinical Anticedents to Clinical In-Hospital Cardiopulmonary Arrest, *Chest*, vol. 98, No. 6, pp. 1388-1392, 1990.

Schmidt-Notwara, Wolfgang, et al., Oral Appliances for the Treatment of Snoring and Obstructive Sleep Apnea: A Review, An American Sleep Disorders Association Review, Sleep, vol. 18, No. 6, pp. 501-510, 1995, American Sleep Disorders Association and Sleep Research Society.

Schnader, Jeff, Increase of Pulmonary Artery Occlusion Pressure During Upper Airway Obstruction in Sleep Apnea, Case Reports, Critical Care Medicine, 1996, vol. 24, No. 2, pp. 354-358.

Schnapp, Lynn M., et al., Pulse Oximetry Uses and Abuses, Critical Care, Chest, vol. 98, No. 5, Nov. 1990, pp. 1244-1250.

Schneider, H., et al., Neural and local effects of hypoxia on cardiovascular responses to obstructive apnea, Journal Appl Physiol., Mar. 2000, vol. 88, No. 3, pp. 1093-1092 (Abstract).

Schoenberg, R., et al., Making ICU Alarms Meaningful: A Comparison of Traditional vs. Trend-Based Algorithms, AMIA 1999, Annual Symposium (Abstract).

Schwab, Richard J., et al., Upper Airway and Soft Tissue Structural Changes Induced by CPAP in Normal Subjects, American Journal Respiratory Critical Care Medicine, 1996, vol. 154, pp. 1106-1116.

Senn, Oliver et al., Monitoring Carbon Dioxide Tension and Arterial Oxygen Saturation by a Single Earlobe Sensor in Patients With Critical Illness or Sleep Apnea, Chest 2005, vol. 128, pp. 1291-1296, Northbrook, IL, USA.

Series et al., Utility of Nocturnal Home Oximetry for Case Finding in Patients with Suspected Sleep apnea Hypopnea Syndrome, Sep. 15, 1993, Annals of Internal Medicine, col. 119, pp. 449-453.

Series, et al., Influence of Continuous Positive Airways Pressure on Sleep Apnea-Related Desaturation in Sleep Apnea Patients, Lung, 1992; 170: pp. 281-290.

Series, Frederic, et al., Prospective Evaluation of Nocturnal Oximetry for Detection of Sleep-Related Breathing Disturbances in Patients With Chronic Heart Failure, Chest 2005, vol. 127, pp. 1507-1514, Northbrook, IL, USA.

Severinghaus, John W., et al., Recent Developments in Pulse Oximetry, Anesthesiology, vol. 76, pp. 1018-1038, 1992.

Shamir, M. et al., Pulse oximetry plethsymographic waveform during changes in blood volume, British Journal of Anaesthesia, vol. 82(2), pp. 178-181, 1999, Great Britain.

Shepard, J., Gas Exchange and Hemodynamics During Sleep, Medical Clinics of North America, vol. 69, No. 6, Nov. 1985, pp. 1243-1265.

Shephard, John W. Jr., et al., Relationship of Ventricular Ectopy to Oxyhemoglobin Desaturation in Patients with Obstructive Sleep Apnea, Chest, vol. 88, No. 3, Sep. 1985, pp. 335-340, Northbrook, IL, USA.

Shephard, John W., Jr., et al., Uvulopalatopharyngoplasty for Treatment of Obstructive Sleep Apnea, Mayo Clinic Proceedings, vol. 65, pp. 1260-1267, 1990.

Sher, Aaron E., et al., The Efficacy of Surgical Modifications of the Upper Airway in Adults With Obstructive Sleep Apnea Syndrome, An American Sleep Disorders Association Review, Sleep, vol. 19, No. 2, pp. 156-177, Nov. 1995.

Shinohara, E., et al., Visceral Fat Accumulation as an Important Risk Factor for Obstructive Sleep Apnoea Syndrome in Obese Subjects, Journal of Internal Medicine, vol. 241, pp. 11-18, Publisher: Blackwell Science Ltd., 1997.

Shoemaker, W. C. et al., Incidence, Physiologic Description, Compensatory Mechanisms, and Therapeutic Implications of Monitored Events, Critical Care Medicine, Dec. 1989, vol. 17, No. 12, pp. 1277-1285.

Shoemaker, W. C. et al., Multicenter study of noninvasive monitoring systems as alternatives to invasive monitoring of acutely ill emergency patients, Chest, 1998; vol. 114; pp. 1643-1652.

Shoemaker, W. C. et al., Noninvasive Physiologic Monitoring of High-Risk Surgical Patients, Archives of Surgery, vol. 131, No. 7, Jul. 1996, pp. 732-737.

Shoemaker, W. C. et al., Prediction of Outcome and Severity of Illness by Analysis of the Frequency Distributions of Cardiorespiratory Variables, Critical Care Medicine, vol. 5, No. 2, Mar.-Apr. 1977, pp. 82-88.

Shoemaker, W. C. et al., Sequence of Physiologic Patterns in Surgical Septic Shock, Critical Care Medicine, Dec. 21, 1993 (12): pp. 1821.

Shoemaker, W. C., Cardiorespiratory Patterns in Complicated and Uncomplicated Septic Shock: Physiologic Alterations and Their Therapeutic Implications, Ann. Surg., Jul. 1971, vol. 174, No. 1, pp. 119-125.

Shoemaker, W. C., Early Physiologic Patterns in Acurate Illness and Accidents: Toward a Concept of Circulatory Dysfunction and Shock Based on Invasive and Noninvasive Hemodynamic Monitoring, New Horizons, Nov. 1996, vol. 4, No. 4, pp. 395-412.

Shoemaker, W. C., Temporal Physiologic Patterns of Shock and Circulatory Dysfunction Based on Early Descriptions by Invasive and Noninvasive Monitoring, New Horizons, vol. 4, No. 2, May 1996, pp. 300-318.

Shoemaker, W.C., Oxygen Transport and Oxygen Metabolism in Shock and Critical Illness, Invasive and Noninvasive Monitoring of Circulatory Dysfunction and Shock, Critical Care Clinics, vol. 12, No. 4, Oct. 1996, pp. 939-969.

Siggaard-Andersen O. et al., *The Bohr Effect and the Haldane Effect*; Scand J Clin Lab Invest; vol. 3 (1); 1973; pp. 1-8.

(56) References Cited

OTHER PUBLICATIONS

Silverberg, D. S., et al., Essential and Secondary Hypertension and Sleep-Disordered Breathing: A Unifying Hypothesis, Journal of Human Hypertension, 1996, vol. 10, pp. 353-363.

Silverberg, D., et al., Sleep apnoea and hypertension. Active approach to detection of obstructive sleep apnoea is imperative, BMJ, Jul. 2000, vol. 22, pp. 321 (Abstract).

Silverberg, Donald, The Joint National Committee on Prevention, Detection, Evaluation, and Treatment of High Blood Pressure and Obstructive Sleep Apnea: Let Their Silence Not Be Matched by the Silence of the Ordinary Physician, Arch Intern Med., Jun. 8, 1998, vol. 158, pp. 1272-1273.

Simmons, Richard L. et al.; *The Role of the Central Nervous System in Septic Shock: II. Hemodynamic, Respiratory and Metabolic Effects of Intracisternal or Intraventricular Endotoxin*; Annals of Surgery; Feb. 1968; pp. 158-167.

Sin, D. D., et al., Effects of continuous positive airway pressure on cardiovascular outcomes in heart failure patients with and without Cheyne-Stokes respiration, Circulation, Jul. 2000, vol. 102, No. 1, pp. 61-66 (Abstract).

Sinex, James E.; *Pulse Oximetry: Principles and Limitations*; American Journal of Emergency Medicine; vol. 17, No. 1; Jan. 1999; pp. 59-66.

Skjodt, N. M., et al., Screening for hypothyroidism in sleep apnea, American Journal of Respiratory & Critical Care Medicine, vol. 160, No. 2, pp. 732-735, Aug. 1999 (Abstract).

Slutsky et al., Quantification of Oxygen Saturation During Episodic Hypoxemia, American Review of Respiratory Disease, 1980; 121: pp. 893-895.

Smith, Philip E. M., et al., Hypoxemia During Sleep in Duchenne Muscular Dystrophy, American Review Respiratory Disorders, 1988, vol. 137, pp. 884-888.

Smyth, Edward, et al., Apneic Oxygenation Associated with Patient-Controlled Analgesia, Journal of Clinical Anesthesia, vol. 10, pp. 499-501, 1998, Publisher: Elsevier Science, Inc., New York, NY, USA.

Soto, F., Cardiovascular manifestations of obstructive sleep apnea. Effects of the treatment, Rev Med Chil., [Article in Spanish], Sep. 1998, vol. 126, No. 9, pp. 1112-1116 (Abstract).

Soubani, Ayman O., *Noninvasive Monitoring of Oxygen and Carbon Dioxide*; American Journal of Emergency Medicine; vol. 19, No. 2, Mar. 2001, pp. 141-146.

Spector, Rosanne, Low-tech Screening for high-risk breathing disorder, http://healthlink.stanford.edu/healthlink/news2/lowtech.thml, Copyright 1996 Stanford University Medical Center News Bureau.

Staniforth, A. D., et al., Nocturnal desaturation in patients with stable heart failure, Heart, Apr. 1998, vol. 79, No. 4, pp. 394-399, United Kingdom.

Stebbens, V. A., Oxygen saturation and breathing patterns in infancy. 1: Full term infants in the second month of life, Arch Dis Child, May 1991, vol. 66, No. 5, pp. 569-573 (Abstract).

Stegman, S. S., et al., Asymptomatic bradyarrhythmias as a marker for sleep apnea: appropriate recognition and treatment may reduce the need for pacemaker therapy, Pacing Clin Electrophysiol, Jun. 1996, vol. 19, No. 6, pp. 899-904 (Abstract).

Stradling, J. R., et al., Automatic Nasal Continuous Positive Airway Pressure Titration in the Laboratory: Patient Outcomes, Thorax, 1997, vol. 52, pp. 72-75.

Stradling, J. R., et al., Predictors and Prevalence of Obstructive Sleep Apnoea and Snoring in 1001 Middle Aged Men, Thorax, 1991, vol. 46, pp. 85-90.

Stradling, John R., et al., Relation between systemic hypertension and sleep hypoxaemia or snoring: analysis in 748 men drawn from general practice, BMJ, vol. 300, Jan. 13, 1990, pp. 75-78.

Strohl et al., Oxygen Saturation During Breath Holding and During Apneas in Sleep, Chest, Feb. 1984: 85, No. 1; pp. 181-186.

Strohl, Kingman P., Consequences of Sleep-Disordered Breathing, Respiratory Care, Apr. 1998, vol. 43, No. 4, pp. 277-282.

Strohl, Kingman P., et al., Physiologic Basis of Therapy for Sleep Apnea, State of Art: Physiologic Basis of Therapy for Sleep Apnea, pp. 791-802.

Sullivan, Colin E., et al., Reversal of Obstructive Sleep Apnoea by Continuous Positive Airway Pressure applied through the Nares, The Lancet, Apr. 18, 1981, pp. 862, 865.

Sullivan, Mary Anna et al., PCA Update, Unexpected Deaths of Patients Receiving Patient-Controlled Analgesia, Nov. 2001.

Svanborg, et al., A Limited diagnostic Investigation for Obstructive Sleep Apnea Syndrome: Oximetry and Static Charge Sensitive Bed, Chest, 1990; 98: pp. 1341-1345.

Svatikova, A., et al., Plasma brain natriuretic peptide in obstructive sleep apnea, American Journal Cardiology, Aug. 15, 2004, vol. 94, No. 4, pp. 529-532 (Abstract).

Szaboova, E., et al., Obstructive Sleep Apnea as a Cause of Dysrhythmia in Sudden Cardiac Death, Bratisl Lek Listy, Jul.-Aug. 1997, vol. 98, No. 7-8, pp. 448-453 (Abstract).

Tan and T. H. Koh, Evaluation of Obstructive Sleep Apnea in Singapore Using Computerized Polygraphic Monitoring, Annals Academy of Medicine, Mar. 1991, vol. 20, No. 2, pp. 196-200.

Tanchaiswad, Waran, Is Sudden Unexplained Nocturnal Death a Breathing Disorder?, Review Article, Psychiatry and Clinical Neurosciences, 1995, vol. 49, pp. 111-114.

Tang, et al.; *Perepheral neural modulation of endotoxin-induced hyperventilation*; Critical Care Medicine; vol. 26, Issue 9; Sep. 1998, pp. 1558-1563.

Tanigawa, T., et al., Screening for sleep-disordered breathing at workplaces, Ind. Health, Jan. 2005, vol. 43, No. 1, pp. 53-57 (Abstract).

Tatevossian, Raymond G., et al., Noninvasive Hemodynamic Monitoring for Early Warning of Adult Respiratory Distress Syndrome in Trauma Patients, Journal of Critical Care, vol. 15, No. 4 (Dec. 2000), pp. 151-159.

Tatevossian, Raymond G., et al., Transcutaneous oxygen and C02 as early warning of tissue hypoxia and hemodynamic shock in critically ill emergency patients ; *Critical Care Med.*; vol. 28, No. 7; pp. 2248-2253 (2000).

Teramoto, S., et al., Does the altered cardiovascular variability associated with obstructive sleep apnea contribute to development of cardiovascular disease in patients with obstructive sleep apnea syndrome?, Circulation, Dec. 21, 1999, vol. 100, No. 25, pp. e136-e137 (Abstract).

Teschler, H., et al., Influence of Moderate Alcohol Consumption on Obstructive Sleep Apnoea with and without AutoSet™ Nasal CPAP Therapy, European Respiratory Journal, 1996, vol. 9, pp. 2371-2377, Printed in United Kingdom.

Teschler, Helmut, et al., Automated Continuous Positive Airway Pressure Titration for Obstructive Sleep Apnea Syndrome, American Journal Respiratory Critical Care Medicine, vol. 154, pp. 734-740, 1996.

The American Sleep Disorders Association Accreditation Committee, Standards for Accreditation of Sleep Disorders Centers, American Sleep Disorders Association, Rochester, MN, Mar. 1997, Revised Edition, pp. 1-17 (p. 16 missing).

Thorpy, Michael J., The Clinical Use of the Multiple Sleep Latency Test, Report From the American sleep Disorders Association, Sleep, vol. 15, No. 3, 1992, pp. 268-276, American Sleep Disorders Association and Sleep Research Society.

Thorpy, Michael, et al., ASDA Standards of Practice, Practice Parameters for the Use of Portable Recording in the Assessment of Obstructive Sleep Apnea, Standards of Practice Committee of the American Sleep Disorders Associate, Sleep, vol. 17, No. 4, pp. 372-377 (1994).

Thorpy, Michael, et al., Practice Parameters for the Treatment of Obstructive Sleep Apnea in Adults: The Efficacy of Surgical Modifications of the Upper Airway, An American Sleep Disorders Association Review, Sleep, vol. 19, No. 2, pp. 152-155, 1996, American Sleep Disorders Association and Sleep Research Society.

Thorpy, Michael, et al., Practice Parameters for the Treatment of Snoring and Obstructive Sleep Apnea with Oral Appliances, An American Sleep Disorders Association and Sleep Research Society, Sleep, vol. 18, No. 6, pp. 511-513, 1995.

(56) References Cited

OTHER PUBLICATIONS

Thorpy, Michael, et al., Practice Parameters for the Use of Actigraphy in the Clinical Assessment of Sleep Disorders, An American Sleep Disorders Association Report, Sleep, vol. 18, No. 4, pp. 285-287, 1995 American Sleep Disorders Association and Sleep Research Society.
Thorpy, Michael, et al., Practice Parameters for the Use of Laser-assisted Uvulopalatoplasty, An American Sleep Disorders Association and Sleep Research Society, Sleep, vol. 17, No. 8, pp. 744-748, 1994.
Thorpy, Michael, et al., Practice Parameters for the Use of Polysomnography in the Evaluation of Insomnia, An American Sleep Disorders Association Report, Sleep, vol. 18, No. 1, pp. 55-57, 1995 American Sleep Disorders Association and Sleep Research Society.
Timms et al., Oxygen Saturation by Oximetry: analysis by Microcomputer, Journal of Polysomnographic Technology, Spring 1988: pp. 13-21.
Timms, et al., and Profox Associates, Inc., Profox for the Bedside, Version 8SP Nov. 1992, Programs for Oximetry [IBM], User's Manual, Nov. 1992, 20 total pages.
Tkacova, R., et al., Continuous positive airway pressure improves nocturnal barareflex sensitivity of patients with heart failure and obstructive sleep apnea., Journal Hypertension, Sep. 2000, vol. 18, No. 9, pp. 1257-1262 (Abstract).
Tkacova, R., et al., Effects of continuous positive airway pressure on obstructive sleep apnea and left ventricular afterload in patients with heart failure, Circulation, 1998, vol. 98, No. 21, pp. 2269-2275 (Abstract).
Tobert, Daren G., et al., Laboratory Medicine and Pathology, New Directions for Pulse Oximetry in Sleep Disorders, Mayo Clinic Proceedings, 1995, vol. 70, pp. 591, Rochester, Minnesota, USA.
Tobin, Martin J., et al., Breathing Abnormalities During Sleep, Arch Intern Med, vol. 143, Jun. 1983, pp. 1221-1228.
Trang, H., et al., [B20] [Poster: 904] Masimo SetR Pulse Oximetry Improves Detection of Sleep Apnea-Related Hypoxemia, Nov. 2, 2001, C: /Masimo/Biblio, p. 1 of 1.
Tremel, F., et al., High prevalence and persistence of sleep apnoea in patients referred for acute left ventricular failure and medically treated over 2 months, European Heart Journal, Aug. 1999, vol. 20, No. 16, pp. 120-129.
Trinder, J., et al., Pathiophysiological interactions of ventilation, arousals, and blood pressure oscillations during Cheyne-Stokes respiration in patients with heart failure, American Journal Respiratory Critical Care Medicine, Sep. 2000, vol. 162, No. 3 Pt. 1, pp. 808-813 (Abstract).
Trupp, R. J. et al., Prevalence of sleep disordered breathing in a heart failure program, Congestive Heart Failure, Sep.-Oct. 2004, vol. 10, No. 5, pp. 217-220 (Abstract).
Trupp, R. J., The heart of sleep: sleep-disordered breathing and heart failure, Journal Cardiovascular Nursing, Nov.-Dec. 2004, vol. 19, No. 6, Suppl, S67-74 (Abstract).
Ullmer, E., et al., Cheyne-stokes respiration or obstructive sleep apnoea: patterns of desaturation, Respiration, 2000, vol. 67, No. 2, p. 203 (Abstract).
VanBoxem, T. J., et al., Prevalence and severity of sleep disordered breathing in a group of morbidly obese patients, Netherlands Journal of Medicine, vol. 54, No. 5, pp. 202-206, May 1999 (Abstract).
VanSlyke, Donald D., et al., Studies of Gas and Electrolyte Equilibria in Blood, pp. 781-798, Journal Biol. Chem., Oct. 1928, vol. 79, No. 2.
V Á zquez, Juan-Carlos, et al.; "Automated Analysis of Digital Oximetry in the Diagnosis of Obstructive Sleep Apnoea," *Thorax*, vol. 55, pp. 302-307; 2000.
Verbraecken, J., et al., Chronic $CO_2$ Drive in Patients with Obstructive Sleep Apnea and Effect of CPAP, Respiration Physiology, vol. 101, pp. 279-287, 1995, Publisher: Elsevier.

Vgontzas, Alexandros N., et al., Obesity Without Sleep Apnea Is Associated with Daytime Sleepiness, Arch Intern Med., Jun. 22, 1998, vol. 158, pp. 1333-1337.
Vidhani, K., et al., Obstructive sleep apnoea syndrome: is this an overlooked cause of desaturation in the immediate postoperative period?, British Journal Anaesth, Apr. 1997, vol. 78, No. 4, pp. 442-443 (Abstract).
Visser, B.F., Pulmonary Diffusion of Carbon Dioxide, Med. Biol. vol. 5, pp. 155-166, Issue 2, Oct. 1960.
Waldhorn, Richard E., Surgical Treatment of Obstructive Sleep Apnea, Is Mandibular Surgery an Advance?, Chest, 1998, vol. 6, Dec. 1990, pp. 1315-1316.
Walker, Regina Paloyan, et al., Uvulopalatopharyngoplasty Versus Laser-Assisted Uvulopalatoplasty for the Treatment of Obstructive Sleep Apnea, Laryngooscope, vol. 107, Jan. 1997, pp. 76-82.
Weber, W., et al., Low-Perfusion Resistant Pulse Oximetry, Abstract Only, Journal of Clinical Monitoring, vol. II, No. 4, Jul. 1995, p. 284.
Weiss, et al., "Computer Assisted Physiologic Monitoring and Stability Assessment in Vascular Surgical Patients Undergoing General Anesthesia—Preliminary Data," Journal of Clinical Monitoring and Computing, 16:107-113, 2000.
Weiss, J. Woodrow, et al., Cardiovascular Morbidity in Obstructive Sleep Apnea, Progress in Cardiovascular Diseases, vol. 41, No. 5, Mar./Apr. 1999, pp. 367-376.
Wessendorft, T. E., et al., Sleep-disordered breathing among patients with first-ever stroke, Journal Neurology, Jan. 2000, vol. 247, No. 1, pp. 41-47 (Abstract only).
West, Peter, et al., Dynamic in Vivo Response Characteristics of Three Oximeters: Hewlett-Packard 47201A, Biox III, and Nellcor N-100, Sleep, vol. 10, No. 3, 1987, pp. 263-271, Raven Press, New York, USA.
Westesson, Per-Lennart, et al., Morbidity after temporomandibular joint arthrography is lower than after removal of lower third molars, Oral Surgery Oral Medical Oral Pathol., 1990, vol. 70, pp. 2-4.
Wheatley, J. R., et al., Mechanical properties of the upper airway, Curr Opin Pulm Medicine, Nov. 1998, vol. 4, No. 6, pp. 363-369 (Abstract).
White, D. P., et al., Assessment of Accuracy and Analysis Time of a Novel Device to Monitor Sleep and Breathing in the Home, Sleep, vol. 18, No. 2, Feb. 1995, pp. 115-126.
White, David P., Pathophysiology of Obstructive Sleep Apnoea, Sleep-Related Breathing Disorder—2, Thorax, 1995, vol. 50, pp. 797-804.
Whitelaw, William A., et al., Clinical Usefulness of Home Oximetry Compared with Polysomnography for Assessment of Sleep Apnea, American Journal Respiratory Critical Care Medicine, vol. 171, pp. 188-193, 2005, Internet address: www.atsjournals.org.
Whitman, R. A., et al., Comparison of the New Masimo SET V3 Technology with a Conventional Pulse Oximeter during Polysomnography, Sleep, 2001, vol. 24, pp. A412 (730.R).
Wiater, A., et al., Polysomnographic Standards for Infants and Children, Somnologie, vol. 4, pp. 39-42, 2000, Berlin—Wien.
Wieczorek, Paul M., et al., Obstructive Sleep Apnea Uncovered After High Spiral Anesthesia: A Case Report, Cardiothoracic Anesthesia, Respiration and Airway, Canadian Journal of Anesthesia, 2005, vol. 52, No. 7, pp. 761-764.
Wilhoit, Stephen C., et al., Comparison of Indices Used to Detect Hypoventilation during Sleep, Respiration, vol. 47, pp. 237-242, 1985.
Wilkins, Robert L., et al., EGAN'S Fundamentals of Respiratory Care, Analysis and Monitoring of Gas Exchange, Book, Eighth Edition, Chapter 16, Section III, Capnography/Capnometry During Mechanical Ventilation, pp. 383-389.
Wilkinson, M. H., et al., Respiration Physiology 101 (1995) pp. 321-331.
Williams, Adrian J., et al., Clinical Value of Polysomnography, The Lancet, vol. 339, May 2, 1992, p. 1113.
Williams, et al., Screening for Sleep Apnea Using Pulse Oximetry and a Clinical Score, Chest, 100/3, Sep. 1991; pp. 631-635.

(56) References Cited

OTHER PUBLICATIONS

Wright, John, et al., Health effects of obstructive sleep apnoea and the effectiveness of continuous positive airways pressure: a systematic review of the research evidence, BMJ, vol. 314, Mar. 22, 1997, pp. 851-860.

Wright, John, et al., Letters, Obstructive Sleep Apnoea, Authors' reply, bmj.com, Jun. 26, 2001.

Wynne, James W., et al., Disordered Breathing and Oxygen Desaturation During Sleep in Patients with Chronic Obstructive Lung Disease (COLD), The American Journal of Medicine, vol. 66, Apr. 1979, pp. 573-579.

Yamakage, M., et al., Changes in respiratory pattern and arterial blood gases during sedation with propofol or midazolam in spinal anesthesia, Journal Clinical Anesth, Aug. 1999, vol. 11, No. 5, pp. 375-379 (Abstract).

Yantis, M. A., Decreasing surgical risks for patients with obstructive sleep apnea, AORN Journal, Jul. 1998, vol. 68, No. 1, pp. 50-55 (Abstract).

Younes, Magdy, et al. Chemical Control Stability in Patients with Obstructive Sleep Apnea, American Journal Respiratory Critical Care Medicine, vol. 163, pp. 1181-1190, 2001.

Young, Terry, et al., The Gender Bias in Sleep Apnea Diagnosis, Are Women Missed Because They Have Different Symptoms?, Original Investigation, Arch Intern Medicine, vol. 156, Nov. 25, 1996, pp. 2445-2451.

Zafar, Subooha, et al., Choice of Oximeter Affects Apnea-Hypopnea Index, Chest, vol. 127/1, Jan. 2005, pp. 80-88, Clinical Investigations, www.chestjournal.org.

Zamarron, C., et al., Oximetry Spectral Analysis in the Diagnosis of Obstructive Sleep Apnoea, Clinical Science, 1999, vol. 97, pp. 467-473, Printed in Great Britain.

Zoccali, Carmine, et al., Nocturnal Hypoxemia, Night-Day Arterial Pressure Changes and Left Ventricular Geometry in Dialysis Patients, Kidney International, vol. 53, 1998, pp. 1078-1084, International Society of Nephrology.

Zucconi, M., et al., An unattended device for sleep-related breathing disorders: validation study in suspected obstructive sleep apnoea syndrome, European Respiratory Journal, 1996, vol. 9, pp. 1251-1256, Printed in United Kingdom.

Zou, Ding, et al., Obstructive Apneic Events Induce Alpha-Receptor Mediated Digital Vasoconstriction, Sleep, vol. 27, No. 3, 2004, pp. 485-489.

\* cited by examiner

METHOD AND SYSTEM FOR CLASSIFICATION OF PHOTO-PLETHYSMOGRAPHICALLY DETECTED RESPIRATORY EFFORT

RELATED APPLICATIONS

This application is a continuation of U.S. patent application Ser. No. 13/757,564, filed Feb. 1, 2013, which is a continuation of U.S. patent application Ser. No. 12/409,685, filed Mar. 24, 2009, now U.S. Pat. No. 8,365,730, which claims priority to U.S. Provisional Application No. 61/070,565, filed Mar. 24, 2008, all of which are incorporated herein by reference in their entireties.

BACKGROUND

The present disclosure relates to enhanced classification of respiratory efforts based on a photo-plethysmographic signal.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of monitoring devices have been developed for monitoring many such physiological characteristics. These monitoring devices often provide doctors and other healthcare personnel with information that facilitates provision of the best possible healthcare for their patients. As a result, such monitoring devices have become a perennial feature of modern medicine.

One technique for monitoring physiological characteristics of a patient is commonly referred to as pulse oximetry, and the devices built based upon pulse oximetry techniques are commonly referred to as pulse oximeters. Pulse oximeters may be used to measure and monitor various blood flow characteristics of a patient. For example, a pulse oximeter may be utilized to monitor the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. A photo-plethysmographic waveform, which corresponds to the cyclic attenuation of optical energy through the patient's tissue, may be generated from the detected light. Additionally, one or more of the above physiological characteristics may be calculated based upon the amount of light absorbed or scattered. More specifically, the light passed through the tissue may be selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

The blood oxygen saturation of a patient in care may be monitored using a pulse oximeter to ensure that the patient consistently gets enough oxygen. However, other factors may also be indicative of the patient's overall respiratory stability.

BRIEF DESCRIPTION OF THE DRAWINGS

A more complete understanding of the present disclosure may be acquired by referring to the following description taken in conjunction with the accompanying drawings. These drawings represent only certain embodiments of the present disclosure.

DETAILED DESCRIPTION

Figure 1:
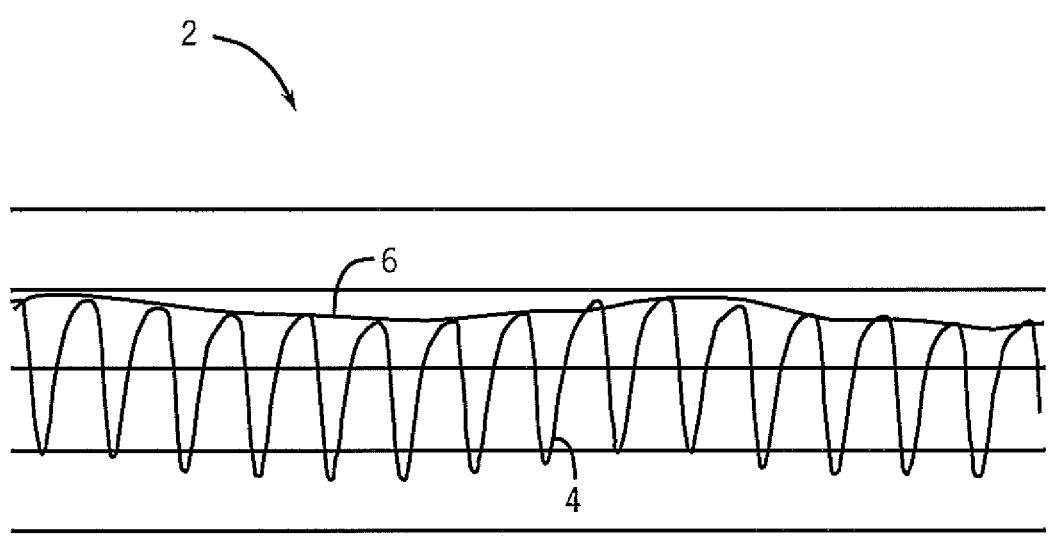
FIG. 1 is an exemplary photo-plethysmographic waveform in accordance with embodiments.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present disclosure may provide a method and system for detecting increased and/or decreased respiratory effort in a patient. Respiratory effort may include a characteristic of a patient's breathing activity relating to the patient's work of breathing, such as respiratory rate, tidal volume, or diaphragmatic pressure. Respiratory effort may synchronously reduce intrathoracic pressure, thereby modulating one or more cardiovascular parameters, including peripheral blood volume, central venous return, cardiac stroke volume, and heart rate.

A pulse oximeter in accordance with present embodiments may be configured to determine the patient's blood oxygen saturation level as well as quantify the patient's respiratory effort. In one embodiment, the respiratory effort may be utilized in conjunction with the blood oxygen saturation to characterize the patient's respiratory stability. For example, obstructive apnea, central apnea, or other underlying respiratory issue causes may be detected based on patterns in the patient's respiratory effort observed in conjunction with the patient's blood oxygen saturation. In another embodiment, an adjusted blood oxygen saturation value may be provided based on the detected respiratory effort. For example, an initial blood oxygen saturation reading may be indexed based on a measured value of respiratory effort.

Additionally, a pulse oximeter in accordance with present embodiments may be used in conjunction with a ventilator to adjust ventilator settings based on the patient's blood oxygen saturation level and/or respiratory effort. For example, the blood oxygen saturation and respiratory efforts of a patient on a respirator may be monitored to ensure that the respirator is operating at optimal conditions. Furthermore, by comparing the patient's measured respiratory effort to the phase or rate of the coupled ventilator, a safety measure may be employed which ensures that no adjustments are made to the ventilator settings if the sensor is applied to a patient who is not using the ventilator. For example, if a caregiver mistakenly places a sensor coupled to a ventilator on a patient other than the patient using the ventilator, present embodiments may identify the caregiver's mistake by comparing respiratory effort to ventilator activity.

In accordance with an exemplary embodiment, arterial blood oxygen saturation, commonly denoted as $SaO_2$, may be estimated as a ratio of oxygenated hemoglobin ($HbO_2$) to deoxygenated hemoglobin (Hb) present in a patient's tissue. Hemoglobin is the component of blood which transports oxygen throughout the body. The ratio of $HbO_2$ to Hb can be determined by shining light at certain wavelengths into a patient's tissue and measuring the absorbance of the light. A first wavelength is typically selected at a point in the electromagnetic spectrum where the absorption of $HbO_2$ differs from the absorption of reduced Hb, and a second wavelength is typically selected at a different point in the spectrum where the absorption of Hb and $HbO_2$ differs from those at the first wavelength. For example, wavelength selections for measuring normal blood oxygenation levels typically include a red light emitted at approximately 660 nm and a near-infrared light emitted at approximately 900 nm, although other red and near-infrared wavelengths may be used. A yellow or orange wavelength may be utilized instead of, or in addition to, the red wavelength.

One common technique for estimating $SaO_2$ is to calculate a characteristic known as the ratio-of-ratios (Ratrat) of the absorption of the red light (RED) to the near-infrared light (IR). While various techniques may be utilized to calculate Ratrat, in one common technique in accordance with an exemplary embodiment, a single sensor is used to emit red and near-infrared light into a patient's tissue and detect the light that is reflected or transmitted. Signals indicative of the detected light are conditioned and processed to generate a photo-plethysmograph of the detected light over time. An exemplary photo-plethysmographic waveform 2 is illustrated in FIG. 1. The waveform 2 is generally periodic, with a high-frequency function 4 representing the pulse rate. This high-frequency function may have both an AC and a DC component which may be estimated from maximum (MAX) and minimum (MIN) points in a cycle of the waveform, according to the following equations:

$$AC = MAX - MIN, \quad (1)$$

$$DC = (MAX + MIN)/2. \quad (2)$$

It should be noted that in other embodiments the maximum and minimum measurements are not necessarily employed to determine the AC and DC components. Indeed, the AC and DC components may be obtained by using essentially any pair of points along both the red and near-infrared light waveforms. The AC and DC components of the RED wavelength and IR wavelength signals may then be used to calculate Ratrat according to the following equation:

$$Ratrat = \frac{AC_{RED}/DC_{RED}}{AC_{IR}/DC_{IR}}. \quad (3)$$

Ratrat has been observed to correlate well to $SaO_2$. This observed correlation is used to estimate $SaO_2$ based on the measured value of the ratio-of-ratios. This pulse-based estimate of $SaO_2$ is commonly denoted as $SpO_2$. An exemplary device for performing these or similar calculations may be the Model N600x pulse oximeter available from Nellcor Puritan Bennett LLC or Covidien.

In addition to the high-frequency function 4 indicative of pulse rate, a low-frequency function 6 corresponding to the patient's respiratory rate may also be present in the waveform 2. The low-frequency function 6 appears on the photo-plethysmographic waveform 2 as a result of the effect of inhalation on heart rate. That is, as the patient inhales, the diaphragm contracts and reduces pressure on the thoracic cavity. This reduced pressure increases the return flow of blood into the veins in the thoracic cavity from peripheral areas of the body and enables the heart to refill faster than it would refill at a higher thoracic pressure. Accordingly, there may be a slight increase in stroke volume and heart rate. When the patient exhales, the pressure in the thoracic cavity again rises. The pressure deviations in the thoracic cavity may be evident in the low-frequency function 6 seen in the waveform 2. Accordingly, respiratory rate or effort may be determined based on the waveform 2 produced utilizing the same sensor used to measure $SpO_2$. For example, the PlethResp™ technology available from CardioDigital Inc. may be utilized to determine the patient's respiratory effort by applying wavelet transform-based technologies to the photo-plethysmographic waveform 2.

As described below, embodiments may include a combination of the detection of the patient's blood oxygen saturation and respiratory effort. In an embodiment, these characteristics may be determined utilizing a pulse oximetry system 10, such as the exemplary system illustrated in FIG. 2. The pulse oximetry system 10 may apply various methods and/or calculations to determine the patient's blood oxygen saturation and/or respiratory effort, and to combine these characteristics for a diagnosis. The system 10 includes a non-invasive sensor 12 and a pulse oximetry monitor 14. The sensor 12 includes an emitter 16 for emitting light at certain wavelengths into a patient's tissue and a detector 18 for detecting the light after it is reflected and/or absorbed by the patient's tissue. The monitor 14 may be configured to calculate physiological parameters received from the sensor 12 relating to light emission and detection. Further, the monitor 14 includes a display 20 configured to display information regarding the physiological parameters, information about the system, and/or alarm indications. The monitor 14 also includes a speaker 22 to provide an audible alarm in the event that the patient's physiological parameters are not within a normal range, as defined based on patient characteristics. The sensor 12 is communicatively coupled to the monitor 14 via a cable 24. However, in other embodiments a wireless transmission device (not shown) or the like may be utilized instead of or in addition to the cable 24.

As indicated by the illustrated embodiment, the pulse oximetry system 10 may include a multi-parameter patient monitor 26. In addition to the monitor 14, or alternatively, the multi-parameter patient monitor 26 may be configured to calculate physiological parameters and to provide a central display 28 for information from the monitor 14 and from other medical monitoring devices or systems (not shown).

For example, the multi-parameter patient monitor 26 may be configured to display a patient's $SpO_2$, pulse rate, and respiratory rate information from the monitor 14 and blood pressure from a blood pressure monitor (not shown) on the display 28. Additionally, the multi-parameter patient monitor 26 may emit a visible or audible alarm via the display 28 or a speaker 30, respectively, if the patient exhibits signs of distress. The monitor 14 may be communicatively coupled to the multi-parameter patient monitor 26 via a cable 32 or 34 coupled to a sensor input port or a digital communications port, respectively. In addition, the monitor 14 and/or the multi-parameter patient monitor 26 may be connected to a network to enable the sharing of information with servers or other workstations (not shown).

Figure 2:
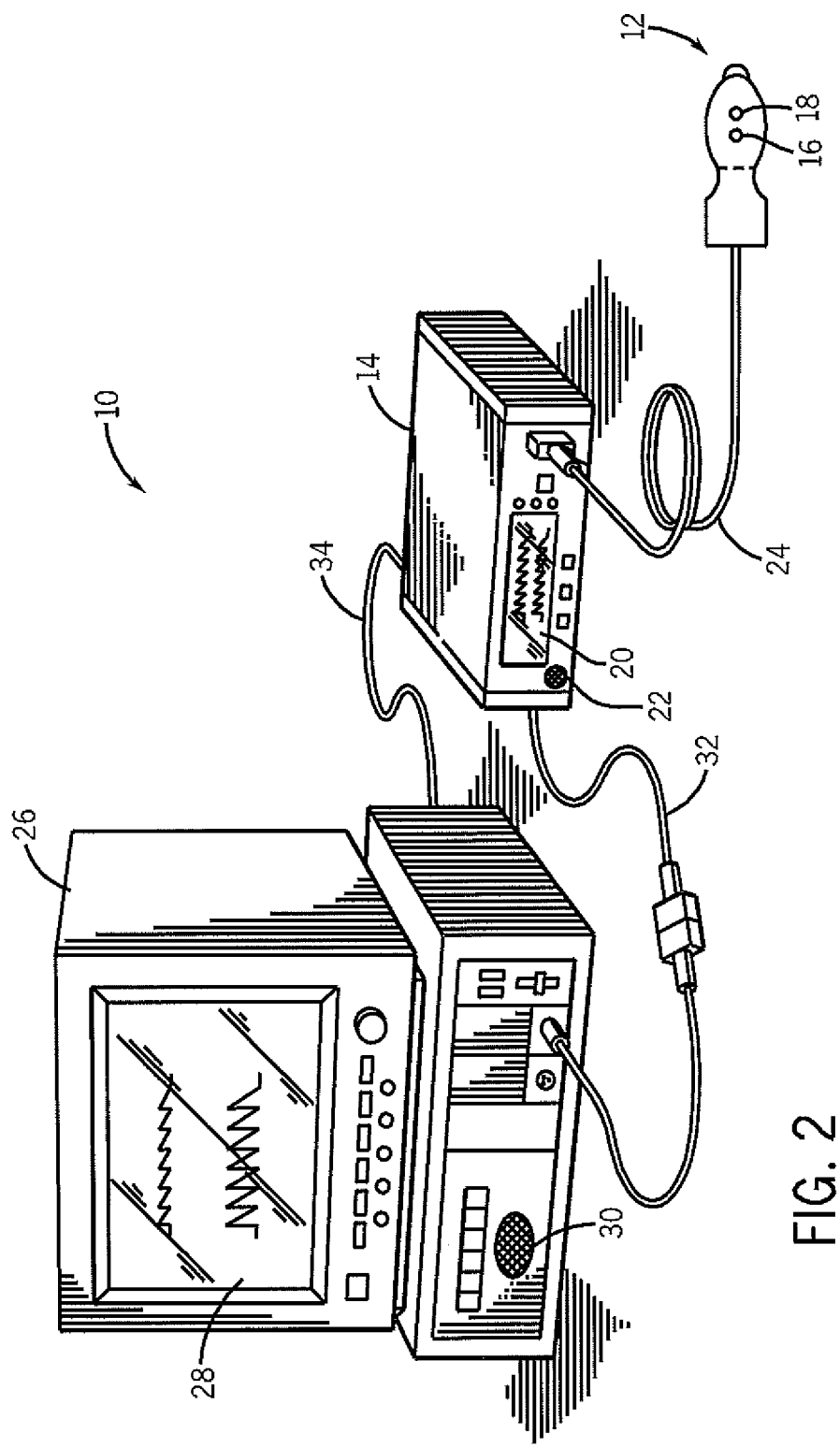
FIG. 2 is a perspective view of a pulse oximeter coupled to a multi-parameter patient monitor and a sensor in accordance with embodiments.
Figure 3:
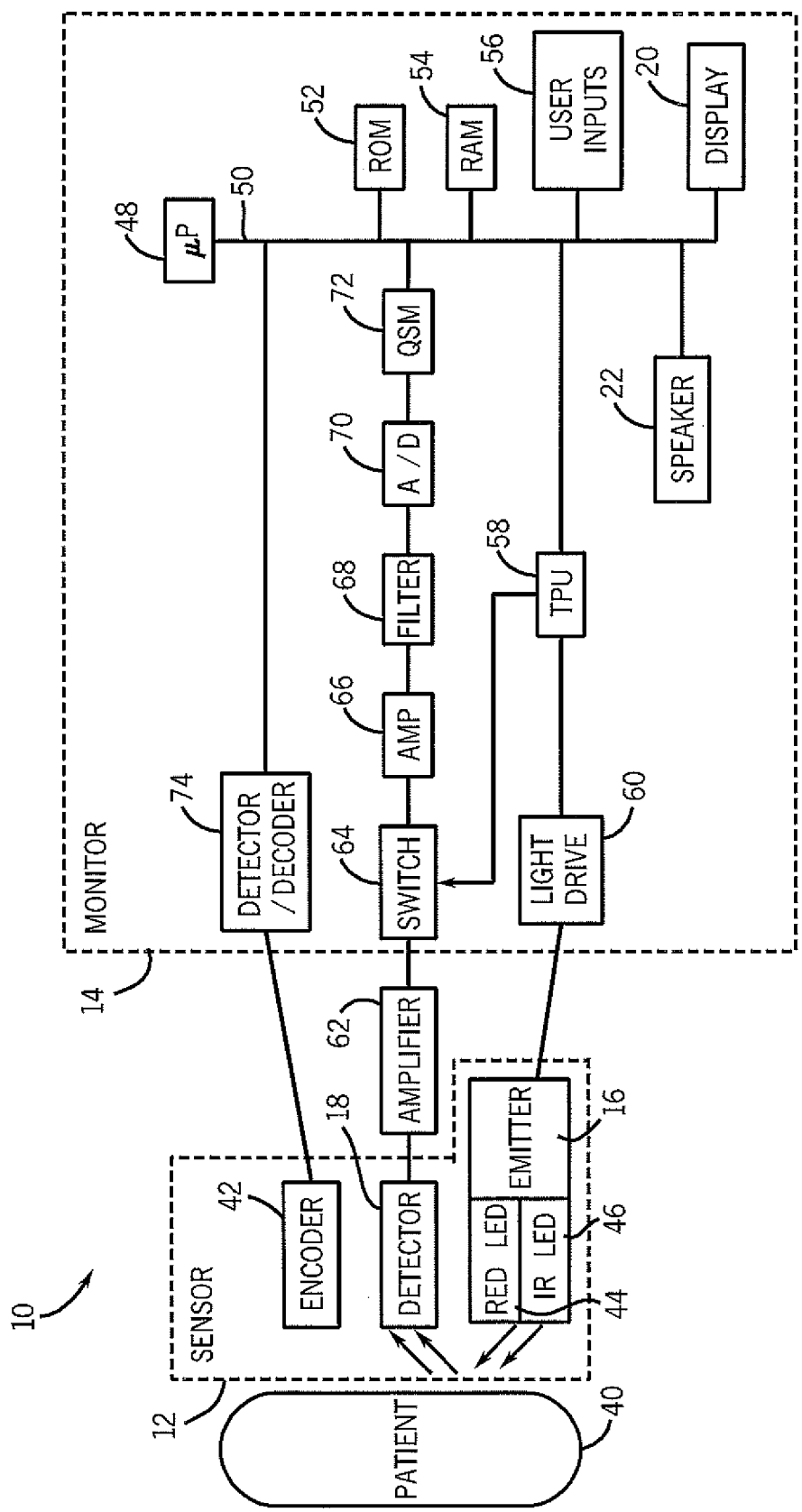
FIG. 3 is a block diagram of the pulse oximeter and sensor coupled to a patient in accordance with embodiments.

FIG. 3 is a block diagram of the exemplary pulse oximetry system 10 of FIG. 2 coupled to a patient 40 in accordance with present embodiments. Specifically, FIG. 3 illustrates certain components of the sensor 12 and the monitor 14 illustrated in FIG. 2. As shown in FIG. 3, the sensor 12 may include the emitter 16, the detector 18, and an encoder 42. In accordance with techniques for producing a photo-plethysmographic waveform, the emitter 16 may be configured to emit at least two wavelengths of light, e.g., RED and IR, into a patient's tissue 40. Hence, the emitter 16 may include a RED LED 44 and an IR LED 46 for emitting light into the patient's tissue 40 at the wavelengths used to calculate the patient's physiological parameters. In certain embodiments, the RED wavelength may be between about 600 nm and about 700 nm, and the IR wavelength may be between about 800 nm and about 1000 nm. Alternative light sources may be used in other embodiments. For example, a single wide-spectrum light source may be used, and the detector 18 may be configured to detect light only at certain wavelengths. In another example, the detector 18 may detect a wide spectrum of wavelengths of light, and the monitor 14 may process only those wavelengths which are of interest. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present techniques.

In one embodiment, the detector 18 may be configured to detect the intensity of light at the RED and IR wavelengths. In operation, light enters the detector 18 after being modulated by the patient's tissue 40. The detector 18 converts the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, the detector 18 sends the signal to the monitor 14, where the photo-plethysmograph waveform may be generated and physiological parameters may be calculated based on the absorption of the RED and IR wavelengths in the patient's tissue 40.

The encoder 42 may contain information about the sensor 12, such as what type of sensor it is (e.g., whether the sensor is intended for placement on a forehead or digit) and the wavelengths of light emitted by the emitter 16. This information may allow the monitor 14 to select appropriate algorithms and/or calibration coefficients for calculating the patient's physiological parameters. The encoder 42 may, for instance, be a coded resistor which stores values corresponding to the type of the sensor 12 and/or the wavelengths of light emitted by the emitter 16. These coded values may be communicated to the monitor 14, which determines how to calculate the patient's physiological parameters. In another embodiment, the encoder 42 may be a memory on which the type of the sensor 12, the wavelengths of light emitted by the emitter 16, and/or the proper calibration coefficients and/or algorithms to be used for calculating the patient's physiological parameters may be stored for communication to the monitor 14.

Signals from the detector 18 and the encoder 42 may be transmitted to the monitor 14. The monitor 14 generally includes a microprocessor 48 connected to an internal bus 50. Also connected to the bus are a read-only memory (ROM) 52, a random access memory (RAM) 54, user inputs 56, the display 20, and the speaker 22. A time processing unit (TPU) 58 provides timing control signals to a light drive circuitry 60 which controls when the emitter 16 is illuminated and the multiplexed timing for the RED LED 44 and the IR LED 46. The TPU 58 also controls the gating-in of signals from detector 18 through an amplifier 62 and a switching circuit 64. These signals are sampled at the proper time, depending upon which light source is illuminated. The received signal from the detector 18 may then be passed through an amplifier 66, a low pass filter 68, and an analog-to-digital converter 70. The digital data may then be stored in a queued serial module (QSM) 72 for later downloading to the RAM 54 as the QSM 72 fills up. In one embodiment, there may be multiple separate parallel paths having the amplifier 66, the filter 68, and the A/D converter 70 for multiple light wavelengths or spectra received.

Signals corresponding to information about the sensor 12 may be transmitted from the encoder 42 to a decoder 74. These signals may include, for example, encoded information relating to the type of the sensor 12 and/or the wavelengths of light emitted by the emitter 16. The decoder 74 may translate these signals to enable the microprocessor 48 to calculate or determine the physiological parameters based on algorithms or look-up tables stored in the ROM 52. In addition, or alternatively, the encoder 42 may contain the algorithms or look-up tables for identifying the physiological parameters. The user inputs 56 may also be used to enter information about the sensor 12.

The microprocessor 48 may then determine the patient's physiological parameters, such as $SpO_2$, pulse rate, respiratory effort, and so forth, based on the values of the received signals corresponding to the light received by the detector 18 (e.g., the photo-plethysmographic waveform) and the information about the sensor 12 from the encoder 42 and/or the user inputs 56. For example, the Model N600x pulse oximeter available from Nellcor Puritan Bennett LLC or Covidien may calculate $SpO_2$ utilizing attenuation signals from two or more wavelengths of light, as described above. Additionally, the PlethRESP™ technology available from CardioDigital Inc., or another method (e.g. time- or frequency-domain detection of changes in pulse rate or photoplethysmographic DC or AC components that are synchronous with the heart rate), may be implemented to determine the patient's respiratory effort. The PlethRESP™ method utilizes wavelet transform-based technologies applied to the photo-plethysmographic waveform produced from the pulse oximetry attenuation signals to determine respiratory effort.

Upon determining a patient's blood oxygen saturation and respiratory effort, various analyses may be performed to characterize the patient's respiratory stability, as described below. Additionally, the non-invasive single-sensor embodiments described herein may be preferable to other techniques utilizing multiple and/or invasive sensors. In an embodiment, apnea may be identified and characterized (i.e., obstructive or central) based on the SpO$_2$ and respiratory effort. Obstructive apnea is generally caused by an obstruction of the airway. For example, in obstructive sleep apnea, the patient's tongue and soft palate may relax too much, thereby closing the throat until the patient is aroused. Because no net airflow occurs with a closed airway, the work performed by the respiratory muscles may result in decreased intrathoracic and lung pressure (and therefore increased intrathoracic and lung pressure variations). As described above, increased pressure variations may amplify the effects that respiration has on the photo-plethysmographic waveform. Such effects may appear similar to large, unobstructed breaths rather than obstructive apnea. Accordingly, it is now recognized that it may be desirable to analyze the patient's respiratory efforts in conjunction with blood oxygen saturation to distinguish obstructive apnea from heavy breathing.

Furthermore, it is now recognized that it may be desirable to distinguish obstructive apnea from central apnea using present embodiments because the treatments associated with each type of apnea may differ. Obstructive apnea may be treated, for example, by positive airway pressure, surgical intervention, or position treatments. In cases of central apnea, the patient's respiratory center in the brain may fail to give the signal to the body to inhale. That is, there is no obstruction preventing the patient from inhaling, but no effort is made to inhale. Central apnea may be treated by positive airway pressure with a spontaneous/time feature which ensures a minimum number of breaths per minute are taken. In addition, central apnea may be treated by administering, adjusting, or withholding some medications.

In some embodiments, apnea may be diagnosed and/or characterized utilizing SpO$_2$ pattern recognition in conjunction with respiratory effort. Such pattern recognition technology may be described, for example, by Dr. Lawrence Lynn in U.S. Pat. Nos. 5,605,151, 5,891,023, 6,223,064, 6,342,039, 6,609,016, 6,748,252, 6,760,608, and 7,081,095, which are hereby incorporated by reference in their entirety for all purposes. For example, if a large increase in the rate and/or amplitude of photo-plethysmographically detected respiratory effort is closely followed by a gradual drop in SpO$_2$, these factors may indicate obstructive apnea. Accordingly, the entire period of increased respiratory effort may be characterized as obstructive apnea. In this context, "closely followed" may include any circulatory delay between the lungs and the site of the pulse oximetry sensor. Such delay may be fairly stable over a period of several minutes and therefore may be predictable. When the obstruction is removed, such as when the patient is aroused, SpO$_2$ may rise quickly, thereby enabling the end of the obstructive period to be accurately identified. In contrast, a period of increased respiratory effort followed by a stable or increasing SpO$_2$ may not be indicative of an obstruction and therefore may not be characterized as apnea. If a history of repetitive increased respiratory effort and desaturation is recognized, subsequent increases in photo-plethysmographically detected respiratory effort that are not long enough to produce significant desaturation may nonetheless be classified as likely obstructive apneic events. Accordingly, apnea may be detected and properly characterized by combining the detection of respiratory effort with blood oxygen saturation in accordance with embodiments of the present disclosure.

Additionally, if a decrease in the rate of respiratory effort is closely followed by a drop in SpO$_2$, this may be indicative of central apnea. Furthermore, both obstructive and central apnea may cause decreases in SpO$_2$ and increases in blood carbon dioxide levels, both of which may accelerate the patient's pulse rate during the apneic event. Accordingly, combined analysis of respiratory effort, SpO$_2$ patterns, and heart rate patterns may enable the monitor 14 to confirm that changes in respiratory effort and SpO$_2$ are due to and indicative of apnea rather than due to some measurement artifact (e.g. motion or electromagnetic interference).

In another embodiment, an increase in respiratory effort may be indicative of an underlying cause, such as impaired alveolar diffusion (e.g., pneumonia), increased airway resistance (e.g., chronic obstructive pulmonary disease (COPD) or asthma), or increased metabolism (e.g., fever). For example, if a large and gradual rise in respiratory effort is accompanied by an increase in heart rate and/or a reduction in SpO$_2$, this may indicate that the increased respiratory effort is the result of an underlying condition rather than an obstruction. In some instances, it may be desirable to produce an indexed SpO$_2$ value which accounts for the patient's increased respiratory effort in producing a blood oxygen saturation value. An example of such an indexed SpO$_2$ value may use the Ventilation Oximetry Index (VOI) described by Dr. Lawrence Lynn in U.S. Pat. Nos. 6,223, 064, 6,342,039, 6,609,016, 6,748,252, and 6,760,608, which are herein incorporated by reference in their entirety for all purposes. The VOI may generally be determined by comparing a patient's actual respiratory effort to an expected respiratory effort based on the patient's SpO$_2$. For example, if the patient is breathing heavily (increased respiratory effort) but the patient's SpO$_2$ is not increasing, this may result in a lower indexed SpO$_2$ value. That is, if the patient were breathing normally, the SpO$_2$ value would be lower than the measured value.

In a further embodiment, combined SpO$_2$ and respiratory effort evaluations may be utilized to adjust parameters of a mechanical ventilator (e.g., triggering, fraction of inspired oxygen (FiO$_2$), positive end-expiratory pressure (PEEP)). For example, where there is a significant delay between the patient's effort to trigger a ventilator breath and when the ventilator triggers the breath, this may result in a pattern of reduced intrathoracic and lung pressure while the patient tries to trigger each ventilator breath, followed by increased intrathoracic and lung pressure during the ventilator's inspiratory phase, therefore causing a pattern of brief periods of accelerated venous return due to the patient's triggering effort followed by reduced venous return during the ventilator's inspiratory phase. This distinctive pattern may be recognized utilizing the techniques described above, and the ventilator triggering may be adjusted accordingly. Such adjustment may be automatic, or the caregiver may be alerted to manually adjust the ventilator triggering.

Furthermore, with regard to ventilators that use SpO$_2$ readings to automatically adjust parameters, it may be desirable to ensure that the pulse oximetry sensor is connected to the appropriate patient (i.e., the patient being ventilated) by comparing the SpO$_2$ reading with the patient's respiratory effort. For example, if a caregiver mistakenly places a sensor that is coupled to a ventilator on a patient other than the one using the ventilator, the present embodiment may prevent changes to the ventilator settings. Accordingly, the respiratory-induced effects on the photo-plethysmographic waveform may be correlated to the phase or rate of the ventilator. The ventilator's respiratory effort increases rather than decreases intrathoracic and lung pressure and therefore the detected circulatory variations may be opposite that observed with diaphragmatic respiration. If the respiratory-induced effects indicated on the waveform do not match the ventilator's respiratory effort, ventilator adjustments may be suspended and/or a notification may be provided to the caregiver to ensure that the sensor is applied to the correct patient.

While embodiments of this disclosure have been depicted, described, and are defined by reference to specific example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A system comprising:
a ventilator configured to be attached to a patient and configured to operate based at least in part on a ventilator setting to generate a desired respiratory effort; and
a monitor configured to:
analyze a plethysmograph signal to determine information corresponding to an actual respiratory effort,
automatically adjust the ventilator setting based on blood oxygen saturation of the patient,
determine whether a desired relationship exists between the information corresponding to the actual respiratory effort and the desired respiratory effort, and
operate the ventilator such that the ventilator adjustments are suspended when the desired relationship is determined not to exist.

2. The system of claim 1 wherein the monitor is further configured to determine whether a relationship exists between a ventilation phase of the ventilator and the actual respiratory effort.

3. The system of claim 1 wherein the monitor is further configured to determine whether a relationship exists between a ventilation rate of the ventilator and the actual respiratory effort.

4. The system of claim 1 wherein the monitor is further configured to generate a sensor placement alarm signal when the desired relationship is determined not to exist.

5. The system of claim 1 wherein the blood oxygen saturation is determined based at least in part on the plethysmograph signal.

6. A processor-implemented method comprising:
operating a ventilator configured to be attached to a patient based at least in part on a ventilator setting to generate a desired respiratory effort;
analyzing a plethysmograph signal to determine information corresponding to an actual respiratory effort;
automatically adjusting the ventilator setting based on blood oxygen saturation of the patient;
determining whether a desired relationship exists between the information corresponding to the actual respiratory effort and the desired respiratory effort; and
operating the ventilator such that ventilator adjustments are suspended when the desired relationship is determined not to exist.

7. The method of claim 6 wherein determining whether a desired relationship exists between the information corresponding to the actual respiratory effort and the desired respiratory effort comprises determining whether a relationship exists between a ventilation phase of the ventilator and the actual respiratory effort.

8. The method of claim 6 wherein determining whether a desired relationship exists between the information corresponding to the actual respiratory effort and the desired respiratory effort comprises determining whether a relationship exists between a ventilation rate of the ventilator and the actual respiratory effort.

9. The method of claim 6 further comprising generating a sensor placement alarm signal when the desired relationship is determined not to exist.

10. The method of claim 6 wherein the blood oxygen saturation is determined based at least in part on the plethysmograph signal.

11. A processor-implemented method for use with a ventilator operable in accordance with a ventilator setting, the processor-implemented method comprising:
calculating a patient's blood oxygen saturation value (SpO2) based on a received plethysmograph signal;
calculating the patient's expected respiratory effort value ($E_{expected}$) based at least in part on the patient's blood oxygen saturation;
determining the patient's actual respiratory effort value ($E_{actual}$);
calculating a ventilation oximetry index (VOI) based on the patient's actual respiratory effort value and the expected respiratory effort value;
providing an output based on the VOI;
determining whether a desired relationship exists between the expected and actual respiratory effort value; and
operating the ventilator such that ventilator adjustments relative to the ventilator setting are suspended when the desired relationship is determined not to exist.

12. The method of claim 11 further comprising:
calculating a predicted carbon dioxide saturation change value (dCO2) based on the patient's actual respiratory effort value and the expected respiratory effort value, wherein the VOI is based on the predicted carbon dioxide saturation change value.

13. The method of claim 12 wherein the dCO2 is calculated according to a formula: $CO2=40-40(E_{expected}/E_{actual})$.

14. The method of claim 13, wherein the VOI is calculated according to a formula: $VOI=SpO2-0.5(dCO2)$.

15. The method of claim 11, wherein the VOI is indicative of the patient's blood oxygen saturation value that would have been calculated if the patient was not breathing abnormally.

16. A monitor for use with a ventilator operable in accordance with a ventilator setting, the monitor configured to:
calculate a patient's blood oxygen saturation value (SpO2) based on a received plethysmograph signal;
calculate the patient's expected respiratory effort value ($E_{expected}$) based at least in part on the patient's blood oxygen saturation;
determine the patient's actual respiratory effort value ($E_{actual}$);
calculate a ventilation oximetry index (VOI) based on the patient's actual respiratory effort value and the expected respiratory effort value;
provide an output based on the VOI;
determine an existence of a desired relationship between the expected and actual respiratory effort value; and
operate the ventilator such that ventilator adjustments relative to the ventilator setting are suspended when the desired relationship is determined not to exist.

17. The monitor of claim 16 that is further configured to:
calculate a predicted carbon dioxide saturation change value (dCO2) based on the patient's actual respiratory effort value and the expected respiratory effort value, wherein the VOI is based on the predicted carbon dioxide saturation change value.

18. The monitor of claim 17 wherein the dC02 is calculated according to a formula: $dC02=40-40(E_{expected}/E_{actual})$.

19. The monitor of claim 18, wherein the VOI is calculated according to a formula: $VOI=Sp02-0.5(dC02)$.

20. The monitor of claim 16, wherein the VOI is indicative of the patient's blood oxygen saturation value that would have been calculated if the patient was not breathing abnormally.

* * * * *